(12) United States Patent
Mehl

(10) Patent No.: US 7,776,535 B2
(45) Date of Patent: Aug. 17, 2010

(54) SITE-SPECIFIC INCORPORATION OF FLUORINATED AMINO ACIDS INTO PROTEINS

(75) Inventor: Ryan A. Mehl, Lancaster, PA (US)

(73) Assignee: Franklin and Marshall College, Lancaster, PA (US)

( * ) Notice: Subject to any disclaimer, the term of this patent is extended or adjusted under 35 U.S.C. 154(b) by 317 days.

(21) Appl. No.: 11/671,036

(22) Filed: Feb. 5, 2007

(65) Prior Publication Data

US 2007/0218483 A1  Sep. 20, 2007

Related U.S. Application Data

(60) Provisional application No. 60/765,639, filed on Feb. 6, 2006.

(51) Int. Cl.
- C12Q 1/68 (2006.01)
- C12P 19/34 (2006.01)
- C12N 9/22 (2006.01)

(52) U.S. Cl. ............... 435/6; 435/91.2; 435/199
(58) Field of Classification Search ............ None
See application file for complete search history.

(56) References Cited

U.S. PATENT DOCUMENTS

| | | | |
|---|---|---|---|
| 5,756,316 A | 5/1998 | Schellenberger | |
| 5,783,431 A | 7/1998 | Peterson et al. | |
| 5,824,485 A | 10/1998 | Thompson et al. | |
| 5,958,672 A | 9/1999 | Short | |
| 6,238,884 B1 | 5/2001 | Short et al. | |
| 6,927,042 B2 | 8/2005 | Schultz et al. | |
| 7,045,337 B2 | 5/2006 | Schultz et al. | |
| 7,083,970 B2 | 8/2006 | Schultz et al. | |
| 7,129,333 B2 | 10/2006 | Schultz et al. | |
| 2003/0082575 A1 | 5/2003 | Schultz et al. | |
| 2003/0108885 A1 | 6/2003 | Schultz et al. | |
| 2004/0198637 A1 | 10/2004 | Schultz et al. | |
| 2004/0265952 A1 | 12/2004 | Deiters et al. | |
| 2005/0009049 A1 | 1/2005 | Chin et al. | |
| 2005/0170404 A1 | 8/2005 | Cho et al. | |
| 2005/0208536 A1 | 9/2005 | Schultz et al. | |
| 2005/0220762 A1 | 10/2005 | Cho et al. | |
| 2005/0227318 A1 | 10/2005 | Alfonta et al. | |
| 2005/0250183 A1 | 11/2005 | Schultz et al. | |
| 2006/0019347 A1 | 1/2006 | Cho et al. | |
| 2006/0063244 A1 | 3/2006 | Schultz et al. | |
| 2006/0068478 A1 | 3/2006 | Schultz et al. | |
| 2006/0073507 A1 | 4/2006 | Deiters et al. | |
| 2006/0110784 A1 | 5/2006 | Deiters et al. | |
| 2006/0134748 A1 | 6/2006 | RajBhandary et al. | |
| 2006/0153860 A1 | 7/2006 | Cho et al. | |
| 2006/0183198 A1 | 8/2006 | Buechler et al. | |
| 2006/0233744 A1 | 10/2006 | Shultz et al. | |
| 2006/0234367 A1 | 10/2006 | Schultz et al. | |
| 2006/0246509 A1 | 11/2006 | Deiters et al. | |

FOREIGN PATENT DOCUMENTS

| | | | |
|---|---|---|---|
| WO | 9601901 | | 1/1996 |
| WO | 9604298 A1 | | 2/1996 |
| WO | 0035915 | | 6/2000 |
| WO | 02085923 A2 | | 10/2002 |
| WO | 02086075 A2 | | 10/2002 |
| WO | 2005038002 A2 | | 4/2005 |
| WO | 2005116237 A2 | | 12/2005 |

OTHER PUBLICATIONS

Drake et al Activation of the phosphosignaling protein CheY. I. Analysis of the phosphorylated conformation by 19F NMR and protein engineering. JBiol. Chem Jun. 25, 1993;268(18):13081-8.*

Gakh et al., "Fluorine as an NMR probe for structural studies of chemical and biological systems", Magn. Reson. Chem, Jun. 16, 2000, 38(7): 551-558.

Kobayashi et al., "Structural basis for orthogonal tRNA specificities of tyrosyl-tRNA synthetases for genetic code expansion", Nat. Struct. Biol., Jun. 2003, 10(6): 425-432.

Sisido et al., "Introduction of specialty functions by the position-specific incorporation of nonnatural amino acids into proteins through four-base codon/anticodon pairs", Appl. Microbiol. Biotechnol., 2001, 57(3): 274-281.

International Search Report for PCT/US2007/003217, Dec. 7, 2007, five pages.

(Continued)

Primary Examiner—Manjunath N Rao
Assistant Examiner—Kagnew H Gebreyesus
(74) Attorney, Agent, or Firm—McNees Wallace & Nurick LLC

(57) ABSTRACT

This invention relates, in part, to newly identified polynucleotides, polypeptides, variants and derivatives thereof; processes for making the polynucleotides and the polypeptides, and their variants and derivatives; and uses of the polynucleotides, polypeptides, variants and derivatives. The invention also relates to compositions of orthogonal aminoacyl-tRNA synthetases, and pairs of orthogonal aminoacyl-tRNA synthetases, and orthogonal tRNAs that incorporate fluorinated amino acids into proteins in response to selector codons. The present invention also includes translation biochemistry methods for site-specific incorporation of fluorinated amino acids, for example, $^{18}F$- or $^{19}F$-labelled amino acids, into proteins or peptides. Such amino acids may be used as an NMR probe for characterizing protein structure, dynamics, and reactivity or for radionuclide imaging (e.g., PET). Fluorinated amino acids may also be used to stabilize proteins or peptides.

9 Claims, 4 Drawing Sheets

OTHER PUBLICATIONS

Jackson et al. "Site-Specific Incorporation of a F-Amino Acid into Proteins as an NMR Probe for Characterizing Protein Structure and Reactivity"—Journal of the American Chemical Society—Jun. 30, 2006, JACS Articles Published on Web Jan. 17, 2007—Contribution from the Department of Chemistry, Franklin and Marshall College.

Jackson et al. "Improving Nature's Enzyme Active Site with Genetically Encoded Unnatural Amino Acids"—Journal of the American Chemical Society—Feb. 23, 2006, JACS Articles Published on Web Aug. 3, 2006—Contribution from the Department of Chemistry, Franklin and Marshall College.

Farrell et al.—"Photo-cross-linking interacting proteins with a genetically encoded benzophenone" Chemistry Department of Franklin and Marshall College—copyright Cold Spring Harbor Laboratory Press—Nature Methods / vol. 2 No. 5/ May 2005.

J.T. Gerig—"Gradient-enhanced proton-fluorine NOE experiments"—Copyright 1999 John Wiley & Sons, Ltd.—University of California, Santa Barbara, Department of Chemistry—Magnetic Resonance in Chemistry.

Anne S. Ulrich—"Solid state 19F NMR methods for studying biomembranes"—Progress in Nuclear Magnetic Resonance Spectroscopy—University of Karlsruhe, Institute of Organic Chemistry, Fritz-Haber-Weg 6, Karlsruhe 76131, Germany, Institute for Instrumental Analysis, Forschungszentrum Karlsruhe, Germany—copyright 2004 Elsevier B.V.

Higuchi et al.—"19F and 1H detection of amyloid B plaques in vivo"—Nature Neuroscience Technical Report—copyright 2005 Nature Publishing Group. vol. 8/ No. 4/ Apr. 2005; pp. 527-533.

Mehta et al.—"Fluorinated Proteins as Potential 19F Magnetic Resonance Imaging and Spectroscopy Agents"—copyright 1997 American Chemical Society; Bioconjugate Chem. 1994, 5, pp. 257-261; Department of Radiology, University of Texas Southwestern Medical Center, Dallas, Texas.

Dr. Michael E. Phelps—"The Power of Molecular Imaging"—PET (Positron Emission Tomography) (date unknown).

Maudsley et al. "The Future of Magnetic Resonance Spectroscopy and Spectroscopic Imaging"—Copyright 1997 The Regents, University of California; From the Magnetic Resonance Unit, Department of Veterans Affairs Medical Center and Departments of Radiology, Medicine, Psychiatry, and Neurology, University of California.

BrightSurf.com Science News and Events—www.brightsurf.com—PET's Molecular Imaging Power May Be Best Indicator for Determining Which Patients Develop Alzheimer's—Oct. 6, 2005; Society of Nuclear Medicine; http://www.brightsurf.com/news/headlines/view.article/php?ArticleID=21265.

Young et al.—"New 18F Radiopharmaceuticals at A&RMC"—Centre for PET, Austin & Repatriation Medical Centre, Heidelberg, VIC (date unknown).

Vaalburg et al.—"Amino Acids for the Measurement of Protein Synthesis In Vivo by PET"—Copyright 1992 Pergamon Press; Nucl. Med. Biol. vol. 19, No. 2, pp. 227-237, 1992 Int. J. Radiat. Appl. Instrum. Part B.

Shimizu et al.—"Tumor Imaging with Anti-CEA Antibody Labeled 19F Emulsion"—Copyright 1987 by Academic Press, Inc.; Magnetic Resonance in Medicine 5, pp. 290-295.

* cited by examiner

```
                          SEQUENCE LISTING

<160> NUMBER OF SEQ ID NOS: 9

<210> SEQ ID NO 1
<211> LENGTH: 6204
<212> TYPE: DNA
<213> ORGANISM: Escherichia coli

<400> SEQUENCE: 1
aagaaaccaa ttgtccatat tgcatcagac attgccgtca ctgcgtcttt tactggctct      60
tctcgctaac caaaccggta acccgggacc aagtttactc atatatacgg acagcggtgc     120
ggactgttgt aactcagaat aagaaatgag gccgctcatg gcgttctgtt gcccgtctca     180
ctggtgaaaa gaaaaacaac cctggcgccg cttctttgag cgaacgatca aaaataagtg     240
gcgccccatc aaaaaaatat tctcaacata aaaaactttg tgtaatactt gtaacgctga     300
gtttacgctt tgaggaatcc cccatggacg aatttgaaat gataaagaga aacacatctg     360
aaattatcag cgaggaagag ttaagagagg tttaaaaaaa agatgaaaaa tctgcttaca     420
taggttttga accaagtggt aaaatacatt tagggcatta tctccaaata aaaagatga     480 ttgatttaca aaatgctgga tttgatataa ttatattgtt ggctgattta cacgcctatt     540
taaaccagaa aggagagttg gatgagatta gaaaaatagg agattataac aaaaaagttt     600
ttgaagcaat ggggttaaag gcaaatatg tttatggaag tgcgttccag cttgataagg      660
attatacact gaatgtctat agattggctt taaaaactac cttaaaaaga gcaagaagga     720
gtatggaact tatagcaaga gaggatgaaa atccaaaggt tgctgaagtt atctatccaa     780
taatgcaggt taatgatatt cattatttag gcgttgatgt tgcagttgga gggatggagc     840
agagaaaaat acacatgtta gcaagggagc ttttaccaaa aaaggttgtt tgtattcaca     900
accctgtctt aacgggtttg gatggagaag gaaagatgag ttcttcaaaa gggaattta     960 tagctgttga tgactctcca gaagagatta gggctaagat aaagaaagca tactgcccag    1020
ctggagttgt tgaaggaaat ccaataatgg agatagctaa atacttcctt gaatatcctt    1080
taaccataaa aaggccagaa aaatttggtg gagatttgac agttaatagc tatgaggagt    1140
tagagagttt atttaaaaat aaggaattgc atccaatgga tttaaaaaat gctgtagctg    1200
aagaacttat aaagatttta gagccaatta gaaagagatt ataactgcag tttcaaacgg    1260
gtaccatatg ggaattcgaa gcttgggccc gaacaaaaac tcatctcaga agaggatctg    1320
aatagcgccg tcgaccatca tcatcatcat cattgagttt aaacggtctc cagcttggct    1380
gttttggcgg atgagagaag attttcagcc tgatacagat taaatcagaa cgcagaagcg    1440
gtctgataaa acagaatttg cctggcggca gtagcgcggt ggtcccacct gaccccatgc    1500
cgaactcaga agtgaaacgc cgtagcgccg atggtagtgt ggggtctccc catgcgagag    1560
tagggaactg ccaggcatca aataaaacga aaggctcagt cgaaagactg gcctttcgt     1620 tttatctgtt gtttgtcggt gaacgctctc ctgagtagga caaatccgcc gggagctgtc    1680
cctcctgttc agctactgac ggggtggtgc gtaacggcaa aagcaccgcc ggacatcagc    1740
```

```
gctagcggag tgtatactgg cttactatgt tggcactgat gagggtgtca gtgaagtgct    1800
tcatgtggca ggagaaaaaa ggctgcaccg gtgcgtcagc agaatatgtg atacaggata    1860
tattccgctt cctcgctcac tgactcgcta cgctcggtcg ttcgactgcg gcgagcggaa    1920
atggcttacg aacggggcgg agatttcctg gaagatgcca ggaagatact taacaggaa     1980 gtgagagggc cgcggcaaag ccgttttttcc ataggctccg ccccctgac aagcatcacg    2040 aaatctgacg ctcaaatcag tggtggcgaa acccgacagg actataaaga taccaggcgt    2100
ttcccctggc ggctccctcg tgcgctctcc tgttcctgcc tttcggttta ccggtgtcat    2160
tccgctgtta tggccgcgtt tgtctcattc cacgcctgac actcagttcc gggtaggcag    2220
ttcgctccaa gctggactgt atgcacgaac ccccgttca gtccgaccgc tgcgccttat     2280
ccggtaacta tcgtcttgag tccaacccgg aaagacatgc aaaagcacca ctggcagcag    2340
ccactggtaa ttgatttaga ggagttagtc ttgaagtcat gcgccggtta aggctaaact    2400
gaaaggacaa gttttggtga ctgcgctcct ccaagccagt tacctcggtt caaagagttg    2460
gtagctcaga gaaccttcga aaaaccgccc tgcaaggcgg ttttttcgtt ttcagagcaa    2520
gagattacgc gcagaccaaa acgatctcaa gaagatcatc ttattaatca gataaaatat    2580
ttctagattt cagtgcaatt tatctcttca aatgtagcac ctgaagtcag ccccatacga    2640
tataagttgt aattctcatg tttgacagct tatcatcgat aagctttaat gcggtagttt    2700
atcacagtta aattgctaac gcagtcaggc accgtgtatg aaatctaaca atgcgctcat    2760
cgtcatcctc ggcaccgtca ccctggatgc tgtaggcata ggcttggtta tgccggtact    2820
gccgggcctc ttgcgggata tcgtccattc cgacagcatc gccagtcact atggcgtgct    2880
gctagcgcta tatgcgttga tgcaatttct atgcgcaccc gttctcggag cactgtccga    2940
ccgctttggc cgccgcccag tcctgctcgc ttcgctactt ggagccacta tcgactacgc    3000
gatcatggcg accacacccg tcctgtggat cctctacgcc ggacgcatcg tggccggcat    3060
caccggcgcc acaggtgcgg ttgctggcgc ctatatcgcc gacatcaccg atggggaaga    3120
tcgggctcgc cacttcgggc tcatgagcgc ttgtttcggc gtgggtatgg tggcaggccc    3180
cgtggccggg ggactgttgg gcgccatctc cttgcatgca ccattccttg cggcggcggt    3240
gctcaacggc ctcaacctac tactgggctg cttcctaatg caggagtcgc ataagggaga    3300
gcgtcgaccg atgcccttga gagccttcaa cccagtcagc tccttccggt gggcgcgggg    3360
catgactatc gtcgccgcac ttatgactgt cttctttatc atgcaactcg taggacaggt    3420
gccggcagcg ctctgggtca ttttcggcga ggaccgcttt cgctggagcg cgacgatgat    3480
cggcctgtcg cttgcggtat tcggaatctt gcacgccctc gctcaagcct tcgtcactgg    3540
tcccgccacc aaacgtttcg gcgagaagca ggccattatc gccggcatgg cggccgacgc    3600
gctgggctac gtcttgctgg cgttcgcgac gcgaggctgg atggccttcc ccattatgat    3660
tcttctcgct tccggcggca tcgggatgcc gcgttgcag gccatgctgt ccaggcaggt     3720
agatgacgac catcagggac agcttcaagg atcgctcgcg gctcttacca gcctaacttc    3780
gatcactgga ccgctgatcg tcacggcgat ttatgccgcc tcggcgagca catggaacgg    3840
gttggcatgg attgtaggcg ccgccctata ccttgtctgc ctccccgcgt tgcgtcgcgg    3900
tgcatggagc cgggccacct cgacctgaat ggaagccggc ggcacctcgc taacggattc    3960
accactccaa gaattggagc caatcaattc ttgcggagaa ctgtgaatgc gcaaaccaac    4020
ccttggcaga acatatccat cgcgtccgcc atctccagca gccgcacgcg gcgcatctcg    4080
ggctccttgc atgcaccatt ccttgcggcg gcggtgctca acggcctcaa cctactactg    4140
```

```
ggctgcttcc taatgcagga gtcgcataag ggagagcgta agcttaaaaa aaatccttag    4200
ctttcgctaa ggatctgcag tggtccggcg ggccggattt gaaccagcga catgcggatc    4260
tagagtccgc cgttctacca ggctgaacta ccgccgggaa ttcagcgtta caagtattac    4320
acaaagtttt ttatgttgag aatattttt tgatggggcg ccacttattt ttgatcgttc     4380
gctcaaagaa gcggcgcaac gccatgagcg gcctcatttc ttattctgag ttacaacagt    4440
ccgcaccgct gtccggtagc tccttccggt gggcgcgggg catgactatc gtcgccgcac    4500
ttatgactgt cttctttatc atgcaactcg taggacaggt gccggcagcg cccaacagtc    4560
ccccggccac ggggcctgcc accataccca cgccgaaaca gcgccctgc accattatgt     4620 tccggatctg catcgcagga tgctgctggc taccctgtgg aacacctaca tctgtattaa    4680
cgaagcgcta accgttttta tcaggctctg ggaggcagaa taaatgatca tatcgtcaat    4740
tattacctcc acggggagag cctgagcaaa ctggcctcag gcatttgaga agcacacggt    4800
cacactgctt ccggtagtca ataaaccggt aaaccagcaa tagacataag cggctattta    4860
acgaccctgc cctgaaccga cgaccgggtc gaatttgctt tcgaatttct gccattcatc    4920
cgcttattat cacttattca ggcgtagcac caggcgttta agggcaccaa taactgcctt    4980
aaaaaaatta cgccccgccc tgccactcat cgcagtgtga ctgggtcatg gctgcgcccc    5040
gacacccgcc aacacccgct gacgcgccct gacgggcttg tctgctcccg gcatccgctt    5100
acagacaagc tgtgaccgtc tccgggagct gcatgtgtca gaggttttca ccgtcatcac    5160
cgaaacgcgc gaggcagcag atcaattcgc gcgcgaaggc gaagcggcat gcataatgtg    5220
cctgtcaaat ggacgaagca gggattctgc aaaccctatg ctactccgtc aagccgtcaa    5280
ttgtctgatt cgttaccaat tatgacaact tgacggctac atcattcact ttttcttcac    5340
aaccggcacg gaactcgctc gggctggccc cggtgcattt tttaaatacc cgcgagaaat    5400
agagttgatc gtcaaaacca acattgcgac cgacggtggc gataggcatc cgggtggtgc    5460
tcaaaagcag cttcgcctgg ctgatacgtt ggtcctcgcg ccagcttaag acgctaatcc    5520
ctaactgctg gcggaaaaga tgtgacagac gcgacggcga caagcaaaca tgctgtgcga    5580
cgctggcgat atcaaaattg ctgtctgcca ggtgatcgct gatgtactga caagcctcgc    5640
gtacccgatt atccatcggt ggatggagcg actcgttaat cgcttccatg cgccgcagta    5700
acaattgctc aagcagattt atcgccagca gctccgaata gcgcccttcc ccttgcccgg    5760
cgttaatgat ttgcccaaac aggtcgctga aatgcggctg gtgcgcttca tccgggcgaa    5820 agaacccgt attggcaaat attgacggcc agttaagcca ttcatgccag taggcgcgcg     5880
gacgaaagta aacccactgg tgataccatt cgcgagcctc cggatgacga ccgtagtgat    5940
gaatctctcc tggcgggaac agcaaaatat cacccggtcg gcaaacaaat tctcgtccct    6000
gatttttcac caccccctga ccgcgaatgg tgagattgag aatataacct ttcattccca    6060
gcggtcggtc gataaaaaaa tcgagataac cgttggcctc aatcggcgtt aaacccgcca    6120
ccagatgggc attaaacgag tatcccggca gcaggggatc atttttgcgct tcagccatac    6180 ttttcatact cccgccattc agag                                           6204
```

<210> SEQ ID NO 2
<211> LENGTH: 921
<212> TYPE: DNA
<213> ORGANISM: Escherichia coli

<400> SEQUENCE: 2

-continued

```
atggacgaat tgaaatgat aaagagaaac acatctgaaa ttatcagcga ggaagagtta      60
agagaggttt taaaaaaga tgaaaatct gctctgatag gttttgaacc aagtggtaaa     120
atacatttag gcattatct ccaaataaaa aagatgattg atttacaaaa tgctggattt     180
gatataatta tagctttggc tgatttacac gcctatttaa accagaaagg agagttggat    240
gagattagaa aaataggaga ttataacaaa aaagttttg aagcaatggg gttaaaggca    300
aaatatgttt atggaagtga atctcatctt gataaggatt atacactgaa tgtctataga   360
ttggctttaa aaactacctt aaaaagagca agaaggagta tggaacttat agcaagagag   420
gatgaaaatc caaaggttgc tgaagttatc tatccaataa tgcaggttaa tgcgattcat   480
tatatgggcg ttgatgttgc agttggaggg atggagcaga aaaaataca catgttagca   540
agggagcttt taccaaaaaa ggttgtttgt attcacaacc ctgtcttaac gggtttggat   600
ggagaaggaa agatgagttc ttcaaagggg aattttatag ctgttgatga ctctccagaa   660
gagattaggg ctaagataaa gaaagcatac tgcccagctg gagttgttga aggaaatcca   720
ataatggaga tagctaaata cttccttgaa tatcctttaa ccataaaaag gccagaaaaa   780
tttggtggag atttgacagt taatagctat gaggagttag agagtttatt taaaaataag   840
gaattgcatc caatggattt aaaaaatgct gtagctgaag aacttataaa gattttagag   900
ccaattagaa agagattata a                                              921
```

<210> SEQ ID NO 3
<211> LENGTH: 306
<212> TYPE: PRT
<213> ORGANISM: Escherichia coli

<400> SEQUENCE: 3

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ala Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Ser His Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Met Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205
```

```
Lys Gly Asn Phe Ile Ala Val Asp Asp Ser Pro Glu Glu Ile Arg Ala
        210                 215                 220
Lys Ile Lys Lys Ala Tyr Cys Pro Ala Gly Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 4
<211> LENGTH: 92
<212> TYPE: DNA
<213> ORGANISM: Escherichia coli

<400> SEQUENCE: 4
tctgcagtgg tccggcgggc cggatttgaa ccagcgacat gcggatctag agtccgccgt    60
tctaccaggc tgaactaccg ccgggaattc ag                                  92

<210> SEQ ID NO 5
<211> LENGTH: 6204
<212> TYPE: DNA
<213> ORGANISM: Escherichia coli

<400> SEQUENCE: 5
aagaaaccaa ttgtccatat tgcatcagac attgccgtca ctgcgtcttt tactggctct      60
tctcgctaac caaaccggta acccgggacc aagtttactc atatatacgg acagcggtgc    120
ggactgttgt aactcagaat aagaaatgag gccgctcatg gcgttctgtt gcccgtctca    180
ctggtgaaaa gaaaaacaac cctggcgccc cttctttgag cgaacgatca aaaataagtg    240
gcgccccatc aaaaaaatat tctcaacata aaaaactttg tgtaatactt gtaacgctga    300
gtttacgctt tgaggaatcc cccatggacg aatttgaaat gataaagaga acacatctg     360
aaattatcag cgaggaagag ttaagagagg ttttaaaaaa agatgaaaaa tctgctggta    420
taggttttga accaagtggt aaaatacatt tagggcatta tctccaaata aaaaagatga    480
ttgatttacg aaatgctgga tttgatataa ttatattgtt ggctgattta cacgcctatt    540
taaaccagaa aggagagttg gatgagatta gaaaaatagg agattataac aaaaaagttt    600
ttgaagcaat ggggttaaag gcaaaatatc tttatggaag tccttttcag cttgataagg    660
attatacact gaatgtctat agattggctt taaaaactac cttaaaaaga gcaagaagga    720
gtatggaact tatagcaaga gaggatgaaa atccaaaggt tgctgaagtt atctatccaa    780
taatgcaggt taatacgagt cattatctgg cgttgatgt tgcagttgga gggatggagc    840
agagaaaaat acacatgtta gcaagggagc ttttaccaaa aaaggttgtt tgtattcaca    900
accctgtctt aacgggtttg gatggagaag gaaagatgag ttcttcaaaa gggaattta     960
tagctgttga tgactctcca gaagagatta gggctaagat aaagaaagca tactgcccag   1020
ctggagttgt tgaaggaaat ccaataatgg agatagctaa atacttcctt gaatatcctt   1080
taaccataaa aaggccagaa aaatttggtg gagatttgac agttaatagc tatgaggagt   1140
```

-continued

```
tagagagttt atttaaaaat aaggaattgc atccaatgga tttaaaaaat gctgtagctg   1200
aagaacttat aaagatttta gagccaatta gaaagagatt ataactgcag tttcaaacgg   1260
gtaccatatg ggaattcgaa gcttgggccc gaacaaaaac tcatctcaga agaggatctg   1320
aatagcgccg tcgaccatca tcatcatcat cattgagttt aaacggtctc cagcttggct   1380
gttttggcgg atgagagaag attttcagcc tgatacagat taaatcagaa cgcagaagcg   1440
gtctgataaa acagaatttg cctggcggca gtagcgcggt ggtcccacct gacccatgc    1500 cgaactcaga agtgaaacgc cgtagcgccg atggtagtgt ggggtctccc catgcgagag   1560
tagggaactg ccaggcatca aataaaacga aaggctcagt cgaaagactg ggcctttcgt   1620
tttatctgtt gtttgtcggt gaacgctctc ctgagtagga caaatccgcc gggagctgtc   1680
cctcctgttc agctactgac ggggtggtgc gtaacggcaa agcaccgcc ggacatcagc    1740 gctagcggag tgtatactgg cttactatgt tggcactgat gagggtgtca gtgaagtgct   1800
tcatgtggca ggagaaaaaa ggctgcaccg gtgcgtcagc agaatatgtg atacaggata   1860
tattccgctt cctcgctcac tgactcgcta cgctcggtcg ttcgactgcg gcgagcggaa   1920
atggcttacg aacggggcgg agatttcctg gaagatgcca ggaagatact taacagggaa   1980
gtgagagggc cgcggcaaag ccgttttttcc ataggctccg ccccctgac aagcatcacg    2040 aaatctgacg ctcaaatcag tggtggcgaa acccgacagg actataaaga taccaggcgt   2100 ttccccctggc ggctccctcg tgcgctctcc tgttcctgcc tttcggttta ccggtgtcat   2160
tccgctgtta tggccgcgtt tgtctcattc cacgcctgac actcagttcc gggtaggcag   2220
ttcgctccaa gctggactgt atgcacgaac ccccgttca gtccgaccgc tgcgccttat    2280
ccggtaacta tcgtcttgag tccaacccgg aaagacatgc aaaagcacca ctggcagcag   2340
ccactggtaa ttgatttaga ggagttagtc ttgaagtcat gcgccggtta aggctaaact   2400
gaaaggacaa gttttggtga ctgcgctcct ccaagccagt tacctcggtt caaagagttg   2460
gtagctcaga gaaccttcga aaaaccgccc tgcaaggcgg ttttttcgtt ttcagagcaa   2520
gagattacgc gcagaccaaa acgatctcaa gaagatcatc ttattaatca gataaaatat   2580
ttctagattt cagtgcaatt tatctcttca aatgtagcac ctgaagtcag ccccatacga   2640
tataagttgt aattctcatg tttgacagct tatcatcgat aagctttaat gcggtagttt   2700
atcacagtta aattgctaac gcagtcaggc accgtgtatg aaatctaaca atgcgctcat   2760
cgtcatcctc ggcaccgtca ccctggatgc tgtaggcata ggcttggtta tgccggtact   2820
gccgggcctc ttgcgggata tcgtccattc cgacagcatc gccagtcact atggcgtgct   2880
gctagcgcta tatgcgttga tgcaatttct atgcgcaccc gttctcggag cactgtccga   2940
ccgctttggc cgccgcccag tcctgctcgc ttcgctactt ggagccacta tcgactacgc   3000
gatcatggcg accacacccg tcctgtggat cctctacgcc ggacgcatcg tggccggcat   3060
caccggcgcc acaggtgcgg ttgctggcgc ctatatcgcc gacatcaccg atggggaaga   3120
tcgggctcgc cacttcgggc tcatgagcgc ttgtttcggc gtgggtatgg tggcaggccc   3180
cgtggccggg ggactgttgg cgccatctcc ttgcatgca ccattccttg cggcggcggt    3240
gctcaacggc ctcaacctac tactgggctg cttcctaatg caggagtcgc ataagggaga   3300
gcgtcgacca tgcccttga gagccttcaa cccagtcagc tccttccggt gggcgcgggg    3360
catgactatc gtcgccgcac ttatgactgt cttctttatc atgcaactcg taggacaggt   3420
gccggcagcg ctctgggtca ttttcggcga ggaccgcttt cgctggagcg cgacgatgat   3480
cggcctgtcg cttgcggtat tcggaatctt gcacgccctc gctcaagcct tcgtcactgg   3540
```

```
tcccgccacc aaacgtttcg gcgagaagca ggccattatc gccggcatgg cggccgacgc    3600
gctgggctac gtcttgctgg cgttcgcgac gcgaggctgg atggccttcc ccattatgat    3660
tcttctcgct tccggcggca tcgggatgcc cgcgttgcag gccatgctgt ccaggcaggt    3720
agatgacgac catcagggac agcttcaagg atcgctcgcg gctcttacca gcctaacttc    3780
gatcactgga ccgctgatcg tcacggcgat ttatgccgcc tcggcgagca catggaacgg    3840
gttggcatgg attgtaggcg ccgccctata ccttgtctgc ctccccgcgt tgcgtcgcgg    3900
tgcatggagc cgggccacct cgacctgaat ggaagccggc ggcacctcgc taacggattc    3960
accactccaa gaattggagc caatcaattc ttgcggagaa ctgtgaatgc gcaaaccaac    4020
ccttggcaga acatatccat cgcgtccgcc atctccagca gccgcacgcg gcgcatctcg    4080
ggctccttgc atgcaccatt ccttgcggcg gcggtgctca acggcctcaa cctactactg    4140
ggctgcttcc taatgcagga gtcgcataag ggagagcgta agcttaaaaa aaatccttag    4200
cttccgctaa ggatctgcag tggtccggcg ggccggattt gaaccagcga catgcggatc    4260
tagagtccgc cgttctacca ggctgaacta ccgccgggaa ttcagcgtta caagtattac    4320
acaaagtttt ttatgttgag aatatttttt tgatggggcg ccacttattt ttgatcgttc    4380
gctcaaagaa gcggcgcaac gccatgagcg gcctcatttc ttattctgag ttacaacagt    4440
ccgcaccgct gtccggtagc tccttccggt gggcgcgggg catgactatc gtcgccgcac    4500
ttatgactgt cttctttatc atgcaactcg taggacaggt gccggcagcg cccaacagtc    4560
ccccggccac ggggcctgcc accataccca cgccgaaaca agcgccctgc accattatgt    4620
tccggatctg catcgcagga tgctgctggc taccctgtgg aacacctaca tctgtattaa    4680
cgaagcgcta accgttttta tcaggctctg ggaggcagaa taaatgatca tatcgtcaat    4740
tattacctcc acggggagag cctgagcaaa ctggcctcag gcatttgaga agcacacggt    4800
cacactgctt ccggtagtca ataaaccggt aaaccagcaa tagacataag cggctattta    4860
acgaccctgc cctgaaccga cgaccgggtc gaatttgctt tcgaatttct gccattcatc    4920
cgcttattat cacttattca ggcgtagcac caggcgttta agggcaccaa taactgcctt    4980
aaaaaaatta cgccccgccc tgccactcat cgcagtgtga ctgggtcatg gctgcgcccc    5040
gacacccgcc aacacccgct gacgcgccct gacgggcttg tctgctcccg gcatccgctt    5100
acagacaagc tgtgaccgtc tccgggagct gcatgtgtca gaggttttca ccgtcatcac    5160
cgaaacgcgc gaggcagcag atcaattcgc gcgcgaaggc gaagcggcat gcataatgtg    5220
cctgtcaaat ggacgaagca gggattctgc aaaccctatg ctactccgtc aagccgtcaa    5280
ttgtctgatt cgttaccaat tatgacaact tgacggctac atcattcact ttttcttcac    5340
aaccggcacg gaactcgctc gggctggccc cggtgcattt tttaaatacc cgcgagaaat    5400
agagttgatc gtcaaaacca acattgcgac cgacggtggc gataggcatc cgggtggtgc    5460
tcaaaagcag cttcgcctgg ctgatacgtt ggtcctcgcg ccagcttaag acgctaatcc    5520
ctaactgctg gcggaaaaga tgtgacagac gcgacggcga caagcaaaca tgctgtgcga    5580
cgctggcgat atcaaaattg ctgtctgcca ggtgatcgct gatgtactga caagcctcgc    5640
gtacccgatt atccatcggt ggatggagcg actcgttaat cgcttccatg cgccgcagta    5700
acaattgctc aagcagattt atcgccagca gctccgaata gcgcccttcc ccttgcccgg    5760
cgttaatgat tgcccaaaac aggtcgctga aatgcggctg gtgcgcttca tccgggcgaa    5820
agaaccccgt attggcaaat attgacggcc agttaagcca ttcatgccag taggcgcgcg    5880
```

```
gacgaaagta aacccactgg tgataccatt cgcgagcctc cggatgacga ccgtagtgat    5940
gaatctctcc tggcgggaac agcaaaatat caccccggtcg gcaaacaaat tctcgtccct    6000
gatttttcac cacccctga ccgcgaatgg tgagattgag aatataaccct ttcattccca    6060 gcggtcggtc gataaaaaaa tcgagataac cgttggcctc aatcggcgtt aaacccgcca    6120
ccagatgggc attaaacgag tatcccggca gcagggatc attttgcgct tcagccatac    6180
ttttcatact cccgccattc agag                                            6204
```

<210> SEQ ID NO 6
<211> LENGTH: 921
<212> TYPE: DNA
<213> ORGANISM: Escherichia coli

<400> SEQUENCE: 6

```
atggacgaat ttgaaatgat aaagagaaac acatctgaaa ttatcagcga ggaagagtta     60
agagaggttt taaaaaaaga tgaaaaatct gctggtatag ttttgaacc aagtggtaaa    120 atacatttag gcattatct ccaaataaaa aagatgattg atttacgaaa tgctggattt    180
gatataatta tattgttggc tgatttacac gcctatttaa accagaaagg agagttggat    240
gagattagaa aataggaga ttataacaaa aaagttttg aagcaatggg gttaaaggca    300
aaatatcttt atggaagtcc tttccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tacgagtcat    480
tatctgggcg ttgatgttgc agttggaggg atggagcaga gaaaaataca catgttagca    540
agggagcttt taccaaaaaa ggttgtttgt attcacaacc ctgtcttaac ggggtttggat    600 ggagaaggaa agatgagttc ttcaaaaggg aatttttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                               921
```

<210> SEQ ID NO 7
<211> LENGTH: 306
<212> TYPE: PRT
<213> ORGANISM: Escherichia coli

<400> SEQUENCE: 7

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Arg Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Leu Tyr Gly Ser Pro Phe Gln Leu Asp Lys
```

-continued

```
                     100                 105                 110
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 8
<211> LENGTH: 306
<212> TYPE: PRT
<213> ORGANISM: Escherichia coli

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Arg Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Leu Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ala His
145                 150                 155                 160
```

```
Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 9
<211> LENGTH: 921
<212> TYPE: DNA
<213> ORGANISM: Escherichia coli

<400> SEQUENCE: 9
atggacgaat tgaaatgat  aaagagaaac acatctgaaa ttatcagcga ggaagagtta      60
agagaggttt taaaaaaga  tgaaaaatct gctggtatag gttttgaacc aagtggtaaa     120
atacatttag gcattatct  ccaaataaaa aagatgattg atttacgaaa tgctggattt     180
gatataatta tagtgttggc tgatttacac gcctatttaa accagaaagg agagttggat     240
gagattagaa aaataggaga ttataacaaa aagttttttg aagcaatggg gttaaaggca     300
aaatatcttt atggaagtcc tttccagctt gataaggatt atacactgaa tgtctataga     360
ttggctttaa aaactacctt aaaaagagca agaaggagta tggaacttat agcaagagag     420
gatgaaaatc caaaggttgc tgaagttatc tatccaataa tgcaggttaa tacggcgcat     480
tatctgggcg ttgatgttgc agttggaggg atggagcaga gaaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatggaga tagctaaata cttccttgaa tatcctttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagattata a                                              921
```

US 7,776,535 B2

SITE-SPECIFIC INCORPORATION OF FLUORINATED AMINO ACIDS INTO PROTEINS

CROSS REFERENCE TO RELATED APPLICATIONS

This application claims the benefit of copending U.S. Provisional Patent Application No. 60/765,639, filed Feb. 6, 2006, incorporated herein by reference.

FIELD OF THE INVENTION

This invention relates, in part, to newly identified polynucleotides, polypeptides, variants and derivatives thereof, processes for making the polynucleotides and the polypeptides, and their variants and derivatives; and uses of the polynucleotides, polypeptides, variants and derivatives. The invention also relates to compositions of orthogonal aminoacyl-tRNA synthetases, and pairs of orthogonal aminoacyl-tRNA synthetases, and orthogonal tRNAs that incorporate fluorinated amino acids into proteins in response to selector codons. The present invention also includes translation biochemistry methods for site-specific incorporation of fluorinated amino acids, for example, $^{18}$F- or $^{19}$F-labelled amino acids, into proteins or peptides. Such amino acids may be used as an NMR probe for characterizing protein structure, dynamics, and reactivity or for radionuclide imaging (e.g., PET). Fluorinated amino acids may also be used to stabilize proteins or peptides.

BACKGROUND OF THE INVENTION

Fluorinated compounds have numerous applications in medicine as therapeutic and diagnostic agents. Fluorine has a van der Waals radius (1.2 Å) similar to hydrogen (1.35 Å), and hydrogen replacement with fluorine typically does not cause significant conformational changes. Fluorinated compounds are often biologically inert. Furthermore, the carbon-fluorine bond strength (460 kJ/mol in $CH_3F$) exceeds that of equivalent C—H bonds.

The high sensitivity of $^{19}$F to surrounding environments, 100% natural abundance and high sensitivity to NMR detection (83% that of $^1$H) has made $^{19}$F NMR spectroscopy useful for investigating protein structure and dynamics. Gerig, *Fluorine NMR of Proteins*, Progress in Nuclear Magnetic Resonance Spectroscopy 26(4), 293-370 (1994). The simplicity of observing hypersensitive $^{19}$F chemical shifts by NMR makes it an exquisite tool for monitoring protein movements resulting from small molecule binding, covalent modification, or protein interactions. Bourret, et al., *Activation of The Phosphosignaling Protein CheY. II. Analysis of Activated Mutants by $^{19}$F NMR and Protein Engineering*, J. Biol. Chem. 268 (18), 13089-96 (1993); Luck, et al., *$^{19}$F NMR Studies of The D-Galactose Chemosensory Receptor. 1. Sugar Binding Yields a Global Structural Change*, Biochemistry 30(17), 4248-56 (1991); Hinds, et al., *$^{19}$F NMR Studies of Conformational Changes Accompanying Cyclic AMP Binding to 3-Fluorophenylalanine-Containing Cyclic AMP Receptor Protein from Escherichia coli*, Biochem. J. 287 (Pt. 2), 627-32 (1992); Luck, et al., *$^{19}$F NMR Studies of The Recombinant Human Transferrin N-Lobe and Three Single Point Mutants*, Magn. Reson. Chem. 35, 477-81 (1997). The ability to uniformly label any single site in a protein in vivo will enable the study of large proteins with unprecedented chemical clarity.

Because $^{19}$F-labeled proteins have also seen interest in solid state membrane protein studies, folding studies, protein stabilization and probing disease states with $^{19}$F MRI, a general method for genetically incorporating a $^{19}$F-label into proteins of any size in *Escherichia coli* would have broad application. See, e.g., Bai, et al., *Side Chain Accessibility and Dynamics in The Molten Globule State of alpha-Lactalbumin: A $^{19}$F-NMR Study*, Biochemistry 39(2), 372-80 (2000); Vaughan, et al., *Difluoromethionine as A Novel $^{19}$F NMR Structural Probe for Internal Amino Acid Packing in Proteins*, J. Am. Chem. Soc. 121(37), 8475-78 (1999); Higuchi, et al., *$^{19}$F and $^1$H MRI Detection of Amyloid beta Plaques in Vivo*, Nat. Neurosci. 8(4), 527-33 (2005); Bann, et al., *Folding and Domain-Domain Interactions of The Chaperone PapD Measured by $^{19}$F NMR*, Biochemistry 43(43), 13775-86 (2004); Hoeltzli, et al., *Refolding of [6-$^{19}$F]Tryptophan-Labeled Escherichia coli Dihydrofolate Reductase in The Presence of Ligand: A Stopped-Flow NMR Spectroscopy Study*, Biochemistry 37(1), 387-98 (1998). Although $^{19}$F NMR is a powerful technique for monitoring protein conformational changes and interactions, the inability to site-specifically introduce fluorine labels into proteins of interest severely limits its applicability. Ulrich, *Solid State $^{19}$F NMR Methods for Studying Biomembranes*, Progress in Nuclear Magnetic Resonance Spectroscopy 46, 1-21 (2003).

Drawbacks of current methods for the incorporation of fluorinated amino acids into proteins are numerous. Semisynthetic incorporation enables high fidelity at specific sites but becomes impractical when medium to large proteins are needed. The use of natural translational machinery to force fluorinated mimics of Tyr, Trp, Phe, Met, and Leu into their natural codons may produce large proteins, but altering all locations of one amino acid simultaneously in large proteins results in structural perturbation and overlapping of $^{19}$F signals. Danielson, et al., *Use of $^{19}$F NMR to Probe Protein Structure and Conformational Changes*, Annu. Rev. Biophys. Biomol. Struct. 25, 163-95 (1996); Vaughan, et al., *Difluoromethionine as A Novel $^{19}$F NMR Structural Probe for Internal Amino Acid Packing in Proteins*, J. Am. Chem. Soc. 121(37), 8475-78 (1999); Feeney, et al., *$^{19}$F Nuclear Magnetic Resonance Chemical Shifts of Fluorine Containing Aliphatic Amino Acids in Proteins: Studies on Lactobacillus casei Dihydrofolate Reductase Containing (2S,4S)-5-Fluoroleucine*, J. Am. Chem. Soc. 118(36), 8700-06 (1996); Duewel, et al., *Incorporation of Trifluoromethionine into A Phage Lysozyme: Implications and A New Marker for Use in Protein $^{19}$F NMR*, Biochemistry, 36(11), 3404-16 (1997). Relying on natural machinery also means that incorporation of fluorinated mimics rarely approaches 90% and they are incorporated at different levels throughout the protein due to variation in codon usage.

A need exists for a reliable method for site-specific incorporation of fluorinated amino acids into proteins that does not suffer from the deficiencies of the prior art.

SUMMARY OF THE INVENTION

In order to add fluorinated amino acids to the genetic code, new orthogonal pairs of an aminoacyl-tRNA synthetase and a tRNA are provided. The new materials function efficiently in the translational machinery, but they are orthogonal to the translation system at issue, meaning that the pairs function independently of the synthetases and tRNAs endogenous to the translation system. Characteristics include a tRNA that decodes or recognizes only a specific codon, e.g., a selector codon, that is not decoded by any endogenous tRNA and an aminoacyl-tRNA synthetase that preferentially aminoacylates (or charges) its complementary tRNA with only a fluorinated amino acid. For example, in *E. coli*, an orthogonal pair includes an aminoacyl-tRNA synthetase that does not substantially aminoacylate any of the endogenous tRNAs, e.g., of which there are 40 in *E. coli*, and an orthogonal tRNA that is not substantially aminoacylated by any of the endogenous synthetases, e.g., of which there are 21 in *E. coli*.

Accordingly, an embodiment of the present invention provides novel orthogonal aminoacyl-tRNA synthetases that preferentially charge an orthogonal tRNA with a fluorinated amino acid. Novel translation systems are provided that produce protein products using the orthogonal aminoacyl-tRNA synthetases and orthogonal tRNAs.

Another embodiment of the invention provides a translation system that includes an orthogonal aminoacyl-tRNA synthetase (O—RS). In an embodiment, the translation system is in a cell, for example, an *E. coli* cell. The O—RS is optionally encoded by one or more nucleic acids in the cell. Similarly, an orthogonal tRNA (O-tRNA) preferentially charged by the O—RS is optionally also encoded by one or more nucleic acids in the cell. In other embodiments, the translation system comprises an in vitro translation system, e.g., a cellular extract. The translation system typically also includes an orthogonal tRNA, e.g., an O-tRNA preferentially charged by the O—RS with a fluorinated amino acid. A vector (e.g., an expression vector) may comprise or encode a nucleic acid according to an embodiment of the invention.

Yet another embodiment of the present invention further provides for a composition comprising an orthogonal aminoacyl-tRNA synthetase, an orthogonal tRNA, and a fluorinated amino acid, wherein the orthogonal aminoacyl-tRNA synthetase is capable of preferentially aminoacylating the orthogonal tRNA with the fluorinated amino acid. In an example embodiment, the orthogonal tRNA and the orthogonal aminoacyl-tRNA synthetase are complementary and the orthogonal aminoacyl-tRNA synthetase recognizes a selector codon. In preferred embodiments, $k_{cat}/K_m$ for aminoacylation of the orthogonal tRNA by the orthogonal aminoacyl-tRNA synthetase with a fluorinated amino acid is higher than $k_{cat}/K_m$ for aminoacylation of the orthogonal tRNA by the orthogonal aminoacyl-tRNA synthetase with a natural amino acid. In another preferred embodiment, the orthogonal aminoacyl-tRNA synthetase aminoacylates the orthogonal tRNA with the fluorinated amino acid at least ten-fold more efficiently than the orthogonal aminoacyl-tRNA synthetase aminoacylates the orthogonal tRNA with a natural amino acid. In yet another preferred embodiment, the orthogonal tRNA is aminoacylated by an endogenous tRNA synthetase of a prokaryotic cell with reduced efficiency as compared to aminoacylation of endogenous tRNA by the endogenous tRNA synthetase.

For example, the orthogonal aminoacyl-tRNA synthetase may be a polypeptide comprising an amino acid sequence as set forth in SEQ ID NO: 3 or SEQ ID NO: 8; a polypeptide encoded by a nucleic acid as set forth in SEQ ID NO: 2 or SEQ ID NO: 9 or a complementary polynucleotide sequence thereof, or a polypeptide encoded by a nucleic acid that hybridizes under highly stringent conditions over substantially an entire length of a polynucleotide sequence as set forth in SEQ ID NO: 2 or SEQ ID NO: 9 or a complementary polynucleotide sequence thereof.

The fluorinated amino acid may be a fluorinated aromatic amino acid, such as fluorinated phenylananine, fluorinated p-methylphenylalanine, or fluorinated p-benzoylphenylalanine, wherein at least one carbon atom of the fluorinated amino acid is substituted with a fluorine atom or a fluorine-substituted lower alkyl group, such as a trifluoromethyl group. The fluorinated amino acid should comprise at least one fluorine atom, such as a $^{19}$F atom or a $^{18}$F atom. The fluorinated amino acid may also comprise a photocrosslinking moiety or a photolabile group. Also disclosed herein are heretofore unknown fluorinated amino acids, which may be used in the methods of the invention.

Another embodiment of the invention includes a method of making a fluorinated protein, including the steps of translating a nucleic acid that encodes a protein in a translation system, wherein the nucleic acid comprises a selector codon, and the translation system comprises an orthogonal tRNA that recognizes the selector codon, a fluorinated amino acid, and an orthogonal aminoacyl-tRNA synthetase that preferentially aminoacylates the orthogonal tRNA with the fluorinated amino acid to thereby produce a fluorinated protein.

In addition, another embodiment of the invention includes a method of determining the structure of a fluorinated protein structure having a fluorinated amino acid at a specified position made by a method of the invention. Structure determination may be accomplished by collecting radiofrequency spectroscopic information from the fluorinated protein in a magnetic field of at least 0.5 Tesla, e.g., MRI or NMR. The invention also includes a method of diagnostic medical imaging comprising administering to a subject in need thereof a composition comprising a fluorinated protein with a fluorinated amino acid at a specified position, followed by magnetic resonance imaging, wherein the fluorinated amino acid comprises at least one $^{19}$F atom. Likewise, the invention includes a method of diagnostic medical imaging comprising administering to a subject in need thereof a composition comprising a fluorinated protein with a fluorinated amino acid at a specified position, followed by positron emission tomography (PET) imaging, wherein the fluorinated amino acid comprises at least one $^{18}$F atom.

In yet another embodiment, the invention includes a composition comprising a polynucleotide sequence that encodes a tRNA as set forth in SEQ ID NO: 4 and a polynucleotide sequence that encodes an orthogonal aminoacyl-tRNA synthetase, wherein the orthogonal aminoacyl-tRNA synthetase is a polypeptide comprising an amino acid sequence as set forth in SEQ ID NO: 3 or SEQ ID NO: 8; a polypeptide encoded by a nucleic acid as set forth in SEQ ID NO: 2 or SEQ ID NO: 9 or a complementary polynucleotide sequence thereof; or a polypeptide encoded by a nucleic acid that hybridizes under highly stringent conditions over substantially an entire length of a polynucleotide sequence as set forth in SEQ ID NO: 2 or SEQ ID NO: 9 or a complementary polynucleotide sequence thereof. Such polynucleotide sequences may be contained within a plasmid, such as set forth in SEQ ID NO: 1.

Another embodiment of the invention pertains to a cell comprising an orthogonal aminoacyl-tRNA synthetase that preferentially aminoacylates an orthogonal tRNA with a fluorinated amino acid in vivo. Such a cell may also include an orthogonal tRNA, a fluorinated amino acid, and a nucleic acid that comprises a polynucleotide that encodes a polypeptide and comprises a selector codon that is recognized by the orthogonal tRNA, wherein the cell synthesizes the polypeptide, and wherein at least one amino acid of the polypeptide comprises a fluorine atom. The selector codon may be a unique three base codon, a nonsense codon, a rare codon, an unnatural codon, or at least a four base codon. Furthermore, the orthogonal aminoacyl-tRNA synthetase and the orthogonal tRNA may be complementary. An example cell is a prokaryotic cell, such as a bacterium, e.g., *Escherichia coli*. Optionally, the cell also includes a nucleic acid that encodes a polypeptide of interest, where the polynucleotide comprises the selector codon that is recognized by the O-tRNA. The cell can also include the protein encoded by the target nucleic acid, which protein comprises the fluorinated amino acid.

The invention also provides a composition comprising a translation system that includes an orthogonal tRNA and an orthogonal aminoacyl-tRNA synthetase that preferentially aminoacylates the orthogonal tRNA with a fluorinated amino acid. In another aspect, the invention includes a plasmid comprising a polynucleotide sequence that encodes an orthogonal aminoacyl-tRNA synthetase, a polynucleotide sequence that encodes an orthogonal tRNA that is complementary to the aminoacyl-tRNA synthetase, and a polynucleotide that encodes an antibiotic resistance gene; wherein the orthogonal aminoacyl-tRNA synthetase is capable of selectively aminoacylating the orthogonal tRNA with a fluorinated amino acid in vivo.

Polynucleotides are also an embodiment of the invention. A polynucleotide of the invention also includes an artificial (e.g., man-made and not naturally occurring) polynucleotide comprising a polynucleotide sequence encoding a polypeptide as set forth in the sequence listing herein, or is complementary to that polynucleotide sequence. A polynucleotide of the invention can also include a nucleic acid that hybridizes to a polynucleotide described herein, under highly stringent conditions, over substantially the entire length of the nucleic acid. The invention also includes artificial polynucleotides that are, e.g., at least 80%, at least 90%, at least 95%, at least 98% or more identical to any of the polynucleotides disclosed herein or a polynucleotide comprising a conservative variation thereof. The invention provides nucleic acids that comprise a unique polynucleotide subsequence selected from the sequences of the O-tRNAs and O—RSs disclosed herein. The unique subsequence is unique as compared to a nucleic acid corresponding to any previously known tRNA or RS nucleic acid sequence. Alignment can be performed using, e.g., BLAST set to default parameters.

Vectors comprising a polynucleotide of the invention are also a feature of the invention. For example, a vector of the invention may include a plasmid, a cosmid, a phage, a virus, an expression vector, or the like. A cell comprising a vector of an embodiment of the invention is also a feature of the invention. In certain embodiments, a vector (e.g., a plasmid, a cosmid, a phage, a virus, etc.) comprises a polynucleotide of the invention. In one embodiment, the vector is an expression vector. In certain embodiments, the expression vector includes a promoter operably linked to one or more of the polynucleotides of the invention. In some embodiments, a cell comprises a vector that includes a polynucleotide of the invention.

Other embodiments of the invention include an isolated polynucleotide comprising a sequence of nucleotides of SEQ ID NO: 2 or SEQ ID NO: 9, or an isolated polynucleotide that is substantially identical to any of the foregoing polynucleotides, or an isolated polynucleotide that hybridizes with any of the foregoing polynucleotides under stringent conditions. Still other embodiments of the invention include an isolated polypeptide comprising a sequence amino acids of SEQ ID NO: 3 or SEQ ID NO: 8, or a conservative variant thereof. Also included in the invention is an isolated nucleic acid comprising a nucleic acid sequence having at least 50% sequence identity to SEQ ID NO: 2 or SEQ ID NO: 9 over a region of at least about 500 residues, wherein the nucleic acid encodes at least one polypeptide having aminoacyl-tRNA synthetase activity. Sequence identity may be determined by analysis with a sequence comparison algorithm or by visual inspection. In still another embodiment, the invention includes a nucleic acid isolate consisting essentially of a DNA sequence encoding an aminoacyl-tRNA synthetase having a polypeptide according to SEQ ID NO: 3 or SEQ ID NO: 8, as well as an expression vector containing a DNA sequence encoding an aminoacyl-tRNA synthetase, wherein the vector is capable of expressing a polypeptide according to SEQ ID NO: 3 or SEQ ID NO: 8 in a transformed microorganism in cell culture. The foregoing polynucleotides and polypeptides may be admixed with a carrier, e.g., an aqueous buffer solution or any salts or biologically acceptable excipients.

Still another embodiment of the invention includes a method of synthesizing an orthogonal aminoacyl-tRNA synthetase comprising one or more steps of substituting a natural amino acid of an unnatural aminoacyl-tRNA synthetase for a different natural amino acid in the same location, where the natural amino acid is proximate to a binding site for a fluorinated amino acid. For example, the amino acid binding domain of an unnatural synthetase may be expanded to better accommodate a fluorinated amino acid by substituting an amino acid of the synthetase polypeptide for a different amino acid that is smaller or of diminished polarity.

Kits are also a feature of the invention. For example, a kit for producing a protein with a fluorinated amino acid at a specified position is provided, where the kit includes an orthogonal tRNA that recognizes a selector codon and an orthogonal aminoacyl-tRNA synthetase, packaged in one or more containers. The kit may further include a fluorinated amino acid, instructional materials for producing the protein, an appropriate cell growth medium, reagents for introducing a target nucleic acid encoding the protein of interest, and the like.

Other features and advantages of the present invention will be apparent from the following more detailed description of preferred embodiments, taken in conjunction with the accompanying drawings and sequence listing, which illustrate by way of example the principles of the invention.

BRIEF DESCRIPTION OF THE SEQUENCE LISTING

Figure 1:
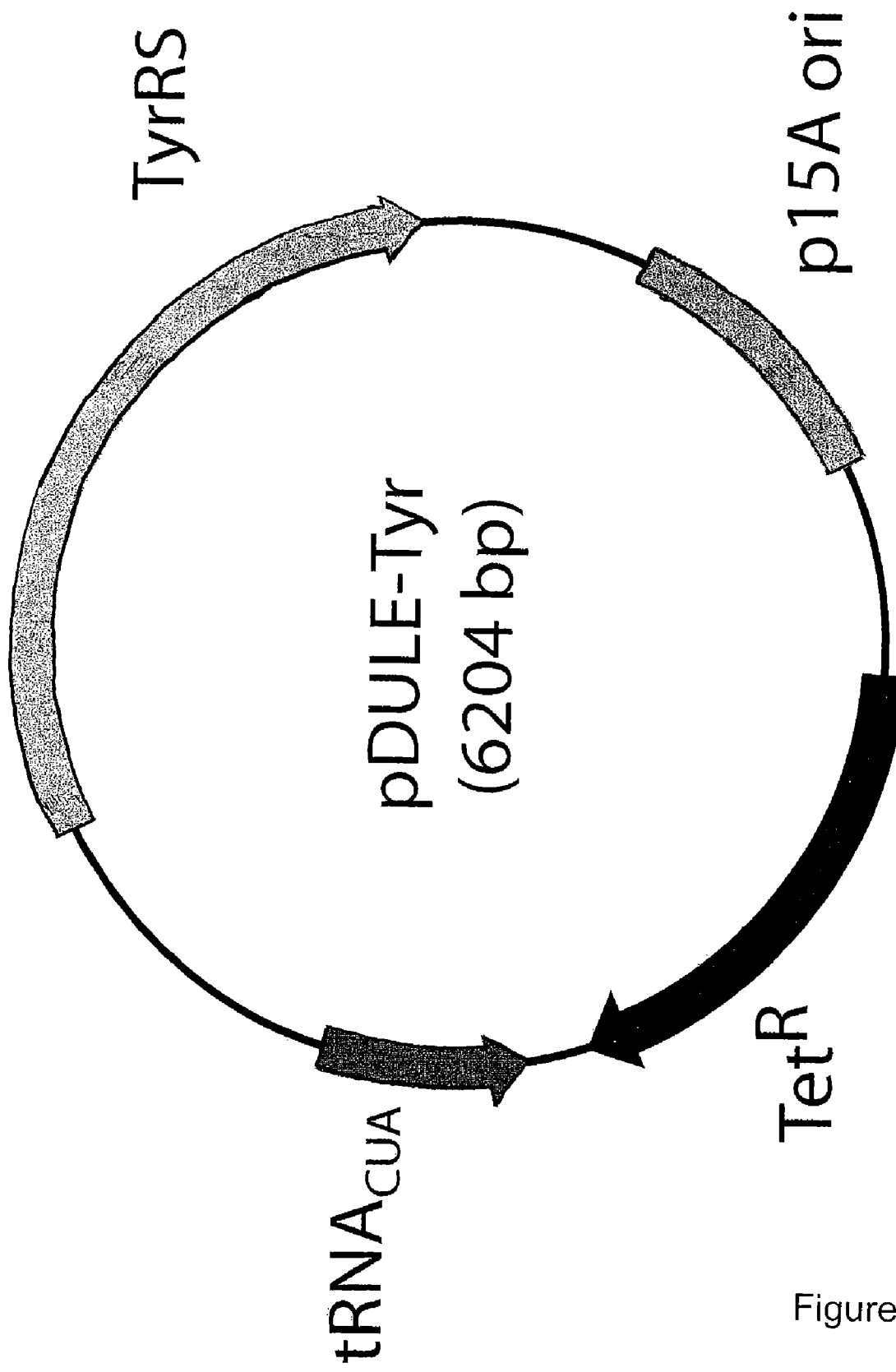
FIG. 1 depicts the DNA plasmid of pDULE-Tyr (SEQ. ID.: 1). The 1pp promotor is located at 248-296, tyrRS at 324-1242, rrnB term at 1381-1676, P15A ori at 1741-2566, $Tet^R$ at 2738-3928, $tRNA_{CUA}$ at 4305-4213 (1pp promotor 4354-4306), and araC at 6178-5300.

SEQ ID NO: 1=pDULE-Tyr plasmid; SEQ ID NO: 2=tfmF-RS gene (DNA); SEQ ID NO: 3=tfmF-RS protein; SEQ ID NO: 4=tRNA gene (DNA); SEQ ID NO: 5=pDULE-pBpa plasmid; SEQ ID NO: 6=pBpa-RS gene (DNA); SEQ ID NO: 7=pBpa-RS protein; SEQ ID NO: 8=pBpa-RS Ser159Ala/Leu65Val mutant protein; and SEQ ID NO: 9=pBpa-RS Ser159Ala/Leu65Val mutant gene (DNA).

DETAILED DESCRIPTION OF THE INVENTION

The practice of the present invention will employ, unless otherwise indicated, conventional techniques of cell biology, cell culture, molecular biology, genetics, microbiology, recombinant DNA, and immunology, which are within the skill of the art. Such techniques are explained fully in the biochemical literature. See, e.g., J. Sambrook, et al., eds., *Genetics; Molecular Cloning A Laboratory Manual, 2nd Ed.*, Cold Spring Harbor Laboratory Press, New York (1989); F. Ausubel, et al., eds., *Short Protocols in Molecular Biology*, 3rd Ed., John Wiley & Sons, Inc., New York (1995); D. N. Glover, ed., *DNA Cloning*, Vol. I-II (1985); M. J. Gait, ed., *Oligonucleotide Synthesis* (1984); Mullis, et al., U.S. Pat. No. 4,683,195; B. D. Hames, S. J. Higgins, eds., *Nucleic Acid Hybridization* (1984); *Methods in Enzymology*, Vol. I, et seq., Academic Press, Inc., London (1955-present); Mayer and Walker, eds., *Immunochemical Methods In Cell And Molecular Biology*, Academic Press, London (1987); D. M. Weir and C. C. Blackwell, eds., *Handbook of Experimental Immunology*, Vol. I-IV (1986); J. Miller, *Experiments in Molecular Genetics*, Cold Spring Harbor Press, New York (1972).

The following illustrative explanations are provided to facilitate understanding of certain terms used frequently herein, particularly in the examples. The explanations are provided as a convenience and are not limitative of the invention.

As used in this specification and the appended claims, the singular forms "a", "an" and "the" include plural referents unless the content clearly dictates otherwise. Thus, for example, reference to "a cell" may include a combination of two or more cells; reference to "bacteria" may include mixtures of bacteria, and the like.

An "orthogonal tRNA" (O-tRNA) is a tRNA that is orthogonal to a translation system of interest. The O-tRNA can exist charged with an amino acid, or in an uncharged state. It will be appreciated that an O-tRNA of the invention is advantageously used to insert essentially any amino acid, whether natural or unnatural, into a growing polypeptide, during translation, in response to a selector codon. An orthogonal tRNA of the invention desirably mediates incorporation of a fluorinated amino acid into a protein that is encoded by a polynucleotide that comprises a selector codon that is recognized by the O-tRNA, e.g., in vivo or in vitro. General methods of producing a recombinant orthogonal tRNA have been described and can be found in, e.g., WO 2002/086075, WO 2005/116237, WO 2005/038002, and WO 2002/085923.

An "orthogonal aminoacyl-tRNA synthetase" (O—RS) is an enzyme that preferentially aminoacylates an O-tRNA with an amino acid in a translation system of interest. Referring to the enzymatic activity of a synthetase, "$K_m$", also known as the Michaelis constant, is the concentration of substrate needed to reach half maximum velocity of the enzyme-catalyzed reaction and is a measure of substrate affinity; and "$k_{cat}$", also known as the turnover number of the enzyme, is related to the maximum number of substrate molecules converted to product per unit of time. The second order rate constant "$k_{cat}/K_m$" indicates the catalytic efficiency of the enzyme and is the second order rate constant for the reaction of enzyme and substrate.

The term "orthogonal" refers to a molecule, e.g., an orthogonal tRNA (O-tRNA) or an orthogonal aminoacyl-tRNA synthetase (O—RS) that functions with endogenous components of a cell or other translation system with reduced efficiency as compared to a corresponding molecule that is endogenous to the cell or translation system or that fails to function when paired with endogenous components of the cell or translation system. In the context of tRNAs and aminoacyl-tRNA synthetases, orthogonal refers to an inability or reduced efficiency (e.g., less than 20% efficiency, less than 10% efficiency, less than 5% efficiency, or less than 1% efficiency) of an orthogonal tRNA to function with an endogenous tRNA synthetase compared to the ability of an appropriate (e.g., homologous or analogous) endogenous tRNA to function when paired with the endogenous complementary tRNA synthetase; or of an orthogonal aminoacyl-tRNA synthetase to function with an endogenous tRNA as compared to the ability of an appropriate endogenous tRNA synthetase to function when paired with the endogenous complementary tRNA.

An "orthogonal" molecule lacks a functionally normal, naturally occurring endogenous complementary molecule in the cell or translation system. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA in a cell of interest with reduced or even undetectable efficiency, as compared to aminoacylation of the endogenous tRNA by a complementary endogenous RS. A second orthogonal molecule can be introduced into the cell that functions when paired with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding (e.g., analogous) tRNA/RS endogenous pair, or an active orthogonal pair.

The term "complementary" refers to components that function together, e.g., an orthogonal tRNA and an orthogonal aminoacyl-tRNA synthetase that preferentially aminoacylates the orthogonal tRNA. An O—RS "preferentially aminoacylates" a O-tRNA when the O—RS charges the O-tRNA with an amino acid more efficiently than it charges any endogenous tRNA in an expression system. That is, when the O-tRNA and any given endogenous tRNA are present in a translation system in approximately equal molar ratios, the O—RS will charge the O-tRNA more frequently than it will charge the endogenous tRNA. Preferably, the relative ratio of O-tRNA charged by the O—RS to endogenous tRNA charged by the O—RS is high, preferably resulting in the O—RS charging the O-tRNA exclusively, or nearly exclusively, when the O-tRNA and endogenous tRNA are present in equal molar concentrations in the translation system. The relative ratio between O-tRNA and endogenous tRNA that is charged by the O—RS, when the O-tRNA and O—RS are present at equal molar concentrations, is greater than 1:1, preferably at least about 2:1, more preferably 5:1, still more preferably 10:1, yet more preferably 20:1, still more preferably 50:1, yet more preferably 75:1, and still more preferably 95:1, 98:1, 99:1, 100:1, 500:1, 1000:1, 5000:1 or higher.

The term "selector codon" refers to a codon recognized by the O-tRNA in the translation process and not typically recognized by an endogenous tRNA. The O-tRNA anticodon loop recognizes the selector codon on the mRNA and incorporates its amino acid, e.g., a fluorinated amino acid, at this site in the polypeptide. Selector codons can include, e.g., nonsense codons, such as stop codons (e.g., amber, ochre, and opal codons), four or more base codons, rare codons, codons derived from natural or unnatural base pairs, or the like.

In general, when an orthogonal pair recognizes a selector codon and loads an amino acid in response to the selector codon, the orthogonal pair is said to "suppress" the selector codon. That is, a selector codon that is not recognized by the translation system's (e.g., cell's) endogenous machinery is not ordinarily translated, which results in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a complementary synthetase in response to a selector codon as compared to an O-tRNA comprising or encoded by a polynucleotide sequence as set forth herein. The translation system (e.g., cell) uses the O-tRNA/O—RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. An anticodon loop of the O-tRNA may recognize the selector codon on an mRNA and incorporate its fluorinated amino acid at the corresponding site in the polypeptide.

Selector codons of the invention expand the genetic codon framework of the protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon (e.g., AGGA), a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple different unnatural amino acids, using these different selector codons. Similarly, more than one copy of a given selector codon can by introduced into a desired gene to allow the site-specific incorporation of a given unnatural amino acid at multiple sites (e.g., two or more, three or more, etc.). For example, a stop codon may be used as a selector codon for the incorporation of a fluorinated amino acid, in which case an O-tRNA may be produced that recognizes a stop selector codon and is aminoacylated by an O—RS with a fluorinated amino acid.

Conventional site-directed mutagenesis can be used to introduce the selector codon at the site of interest in a target polynucleotide encoding a polypeptide of interest. When the O—RS, O-tRNA and the nucleic acid that encodes a polypeptide of interest are combined, e.g., in vivo, the fluorinated amino acid is incorporated in response to the selector codon to give a polypeptide containing the fluorinated amino acid at the specified position.

The incorporation of fluorinated amino acids in vivo can be done without significant perturbation of the host cell. For example, in non-eukaryotic cells, such as *Escherichia coli*, because the suppression efficiency of a stop selector codon, e.g., the UAG codon, depends upon the competition between the O-tRNA, e.g., the amber suppressor tRNA, and release factor 1 (RF1), which binds to the UAG codon and initiates release of the growing peptide from the ribosome, the suppression efficiency can be modulated by, e.g., either increasing the expression level of O-tRNA, e.g., the suppressor tRNA, or using an RF1 deficient strain. In eukaryotic cells, because the suppression efficiency for a UAG codon depends upon the competition between the O-tRNA, e.g., the amber suppressor tRNA, and a eukaryotic release factor (e.g., eRF), which binds to a stop codon and initiates release of the growing peptide from the ribosome, the suppression efficiency can be modulated by, e.g., increasing the expression level of O-tRNA, e.g., the suppressor tRNA. In addition, additional compounds can also be present that modulate release factor action, e.g., reducing agents such as dithiothreitol (DTT).

For a given system, a selector codon can also include one of the natural three base codons, where the endogenous system does not use (or rarely uses) the natural base codon. For example, this includes a system that is lacking a tRNA that recognizes the natural three base codon, or a system where the three base codon is a rare codon. Fluorinated amino acids can be encoded with such rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma, et al., Biochemistry 32, 7939 (1993). In this case, the synthetic tRNA competes with the naturally occurring tRNAArg, which exists as a minor species in *Escherichia coli*. In addition, some organisms do not use all triplet codons. An unassigned codon AGA in *Micrococcus luteus* has been used for insertion of amino acids in an in vitro transcription/translation extract.

Selector codons can also comprise extended codons, e.g., four or more base codons, such as four, five, six, or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC, and the like. Methods of the invention can include using extended codons based on frameshift suppression. Four or more base codons can insert, e.g., one or multiple unnatural amino acids into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs that can be adapted for methods and compositions include, e.g., Hirao, et al., *An unnatural base pair for incorporating amino acid analogues into protein*, Nature Biotechnology 20, 177-82 (2002). See also, Wu, et al., J. Am. Chem. Soc. 124, 14626-30 (2002). See also, e.g., Switzer, et al., J. Am. Chem. Soc. 111, 8322 (1989); Piccirilli, et al., Nature 343, 33 (1990); Kool, Curr. Opin. Chem. Biol. 4, 602 (2000); Kool, Curr. Opin. Chem. Biol. 4, 602 (2000); Guckian, et al., Angew. Chem. Int. Ed. Engl. 36, 2825 (1998); McMinn, et al., J. Am. Chem. Soc. 121, 11586 (1999); Ogawa, et al., J. Am. Chem. Soc. 122, 3274 (2000); Ogawa, et al., J. Am. Chem. Soc. 122, 8803 (2000); Tae, et al., J. Am. Chem. Soc. 123, 7439 (2001). Meggers, et al., J. Am. Chem. Soc. 122, 10714 (2000). Because extended codons and unnatural codons are intrinsically orthogonal to natural codons, the methods of the invention can take advantage of this property to generate orthogonal tRNAs.

The term "translation system" refers to the components that incorporate an amino acid into a growing polypeptide chain (protein). Components of a translation system can include, e.g., ribosomes, tRNAs, synthetases, mRNA, and the like. Typical translation systems include cells, such as bacterial cells (e.g., *Escherichia coli*), archeaebacterial cells, eukaryotic cells (e.g., yeast cells, mammalian cells, plant cells, insect cells), or the like. Alternatively, the translation system comprises an in vitro translation system, e.g., a translation extract including a cellular extract. The O-tRNA or the O—RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, or the like. The translation system can also be a cell-free system, e.g., any of a variety of commercially available in vitro transcription/translation systems in combination with an O-tRNA/O—RS pair and a fluorinated amino acid as described herein.

The translation system may optionally include multiple O-tRNA/O—RS pairs, which allow incorporation of more than one unnatural amino acid, e.g., a fluorinated amino acid and another unnatural amino acid. For example, the cell can further include an additional different O-tRNA/O—RS pair and a second unnatural amino acid, where this additional O-tRNA recognizes a second selector codon and this additional O—RS preferentially aminoacylates the O-tRNA with the second unnatural amino acid. For example, a cell that includes an O-tRNA/O—RS pair (where the O-tRNA recognizes, e.g., an amber selector codon) can further comprise a second orthogonal pair, where the second O-tRNA recognizes a different selector codon (e.g., an opal codon, four-base codon, or the like). Desirably, the different orthogonal pairs are derived from different sources, which can facilitate recognition of different selector codons.

The term "eukaryote" refers to organisms belonging to the phylogenetic domain Eucarya, such as animals (e.g., mammals, insects, reptiles, birds, etc.), ciliates, plants (e.g., monocots, dicots, algae, etc.), fungi, yeasts, flagellates, microsporidia, protists, etc. In contrast, "prokaryotes" include unicellular organisms that typically have a single circular chromosome contained within a nucleoid that is not membrane-bound, as well as various plasmids.

The translational components of the invention can be derived from non-eukaryotic organisms. For example, the orthogonal O-tRNA can be derived from a non-eukaryotic organism (or a combination of organisms), e.g., an archaebacterium, such as *Methanococcus jannaschii*, *Methanobacterium thermoautotroplzieum*, Halobacterium such as *Haloferax volcanii* and Halobacterium species NRC-1, *Archaeoglobus fulgidus, Pyrococcus furiosus, Pyrococcus horikoshii, Aeuropyrum pernix, Methanococcus maripaludis, Methanopyrus kandleri, Pyrococcus abyssi, Sulfolobus solfataricus, Sulfolobus tokodaii, Therinoplasma acidophilum, Thermoplasma volcanium*, or the like, or a eubacterium, such as *Escherichia coli, Thermus thermophilus, Bacillus stearothermphilus*, or the like, while the orthogonal O—RS can be derived from a non-eukaryotic organism (or a combination of organisms), e.g., an archaebacterium, such as *Methanococcus jannaschii, Methanobacterium thermoautotrophicum*, Halobacteriuin such as *Haloferax volcanii* and Halobacterium species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O—RSs. The individual components of an O-tRNA/O—RS pair can be derived from the same organism or different organisms. In one embodiment, the O-tRNA/O—RS pair is from the same organism. Alternatively, the O-tRNA and the O—RS of the O-tRNA/O—RS pair are from different organisms.

Host cells are genetically engineered (e.g., transformed, transduced or transfected) with the polynucleotides of the invention or constructs that include a polynucleotide of the invention, e.g., a vector of the invention, which can be, for example, a cloning vector or an expression vector. For example, the coding regions for the orthogonal tRNA, the orthogonal tRNA synthetase and the protein to be derivatized are operably linked to gene expression control elements that are functional in the desired host cell. A cell of the invention provides the ability to synthesize proteins that comprise unnatural amino acids in large useful quantities. In one aspect, the composition optionally includes, e.g., at least about 10 micrograms to about 100 milligrams or more of the protein that comprises a fluorinated amino acid or multiple unnatural amino acids, or an amount that can be achieved with in vivo protein production methods. In another aspect, the protein is optionally present in the composition at a concentration of, e.g., at least about 10 micrograms to about 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one fluorinated amino acid is a feature of the invention.

Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication or integration in prokaryotes, eukaryotes, or preferably both. See, Giliman and Smith, Gene 8, 81 (1979); Roberts, et al., Nature 328, 731 (1987); Schneider, et al., Protein Expr. Purif 6435, 10 (1995). The vector can be, for example, in the form of a plasmid, a bacterium, a virus, a naked polynucleotide, or a conjugated polynucleotide. The vectors are introduced into cells or microorganisms by standard methods including electroporation infection by viral vectors, high velocity ballistic penetration by small particles with the nucleic acid either within the matrix of small beads or particles or on the surface. See, e.g., From, et al., Proc. Natl. Acad. Sci. U.S.A. 82, 5824 (1985); Klein, et al., Nature 327, 70-73 (1987).

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation or protein expression or purification) include Freshney, *Culture of Animal Cells, A Manual of Basic Technique*, 4th Ed., Wiley-Liss, New York (2000), and the references cited therein; Higgins and Hames, Eds., *Protein Expression: A Practical Approach*, Practical Approach Series, Oxford University Press (1999); Shuler, et al., Eds., (1994); *Baculovirus Expression Systems and Biopesticides*, Wiley-Liss; Payne, et al., *Plant Cell and Tissue Culture in Liquid Systems*, John Wiley and Sons, Inc. New York, N.Y. (1992); Gamborg and Phillips, Eds., *Plant Cell, Tissue and Organ Culture* (1995); *Fundamental Methods Springer Lab Manual*, Springer-Verlag, Berlin; Atlas and Parks, Eds., *The Handbook of Microbiological Media* CRC Press, Boca Raton, Fla. (1993).

As used herein, the term "conservative variant", in the context of a translation component, refers to a translation component, e.g., a conservative variant O-tRNA or a conservative variant O—RS, that functionally performs similarly to a base component that the conservative variant is similar to, e.g., an O-tRNA or O—RS, having variations in the sequence as compared to a reference O-tRNA or O—RS. For example, an O—RS will aminoacylate a complementary O-tRNA or a conservative variant O-tRNA with a fluorinated amino acid although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O—RS. For example, conservative variations of an O-tRNA include those molecules that function like the particular O-tRNA, e.g., as in the sequence listing herein, and that maintain the tRNA L-shaped structure by virtue of appropriate self-complementarity, but that do not have a sequence identical to those, e.g., in the sequence listing, figures, or examples herein, and desirably are other than wild type tRNA molecules.

As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. Polynucleotides of the invention are isolated. The term "isolated" includes nucleic acid molecules that are synthesized (e.g., chemically, enzymatically, or recombinantly) or are naturally occurring but separated from other nucleic acid molecules that are present in a natural source of the nucleic acid.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted, or modified. An "amino acid sequence" is a polymer of amino acid residues (a protein, polypeptide, etc.) or a character string representing an amino acid polymer, depending on context.

The term "nucleoside" includes purine and pyrimidine bases that are covalently attached to a sugar moiety, preferably ribose or deoxyribose. Examples of preferred nucleosides include ribonucleosides and deoxyribonucleosides. The term "nucleotide" includes nucleosides that further comprise a phosphate group or a phosphate analog.

The term "polynucleotide" generally refers to any polyribonucleotide or polydeoxyribonucleotide, which may be unmodified RNA or DNA or modified RNA or DNA. Thus, for instance, polynucleotides as used herein refers to, among others, single and double stranded DNA, DNA that is a mixture of single and double stranded regions, single and double stranded RNA, and RNA that is mixture of single and double stranded regions, hybrid molecules comprising DNA and RNA that may be single stranded or, more typically, double stranded or a mixture of single and double stranded regions. In addition, polynucleotide as used herein refers to triple stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple helical region often is an oligonucleotide.

The term "oligonucleotide" refers to a relatively short polynucleotide. Often the term refers to single stranded deoxyribonucleotides, but it can refer as well to single or double stranded ribonucleotides, RNA:DNA hybrids and double stranded DNAs, among others. Oligonucleotides, such as single stranded DNA probe oligonucleotides, often are synthesized by chemical methods, such as those implemented on automated oligonucleotide synthesizers. However, oligonucleotides can be made by a variety of other methods, including in vitro recombinant DNA mediated techniques and by expression of DNAs in cells and organisms.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention optionally comprises or encodes complementary sequences, in addition to any sequence explicitly indicated.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Plasmids generally are designated herein by a lower case "p" preceded or followed by capital letters or numbers, in accordance with standard naming conventions that are familiar to those of skill in the art. Starting plasmids disclosed herein are either commercially available, publicly available on an unrestricted basis, or can be constructed from available plasmids by routine application of art-recognized procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term polynucleotide includes DNAs or RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

The present application is directed to nucleic acid molecules at least 90%, 95%, 96%, 97%, 98% or 99% identical to the nucleic acid sequences disclosed herein irrespective of whether they encode a polypeptide having synthetase activity. This is because even where a particular nucleic acid molecule does not encode a polypeptide synthetase functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having synthetase functional activity include, inter alia, (1) isolating a gene or allelic or splice variants thereof in a cDNA library; (2) in situ hybridization (e.g., "FISH") to metaphase chromosomal spreads to provide precise chromosomal location of genes, as described in Verma, et al., *Human Chromosomes: A Manual of Basic Techniques*, Pergamon Press, New York (1988); and (3) northern blot analysis for detecting mRNA expression in specific tissues.

A "variant" of a polynucleotide or polypeptide, as the term is used herein, includes polynucleotides or polypeptides that differ from a reference polynucleotide or polypeptide, respectively. A polynucleotide variant is a polynucleotide that differs in nucleotide sequence from another, reference polynucleotide. Generally, differences are limited so that the nucleotide sequences of the reference and the variant are closely similar overall and, in many regions, identical. Changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence.

Owing to the degeneracy of the genetic code, "silent substitutions" (i.e., substitutions in a nucleic acid sequence that do not result in an alteration in an encoded polypeptide) are an implied feature of every nucleic acid sequence that encodes an amino acid. Similarly, "conservative amino acid substitutions," in which one or a few amino acids in an amino acid sequence are substituted with different amino acids with highly similar properties, are also readily identified as being highly similar to a disclosed construct. Such conservative variations (or conservative variants) of each disclosed sequence are a feature of the present invention.

"Conservative variants" or "conservative variations" of a particular nucleic acid sequence refers to those nucleic acids that encode identical or essentially identical amino acid sequences, or, where the nucleic acid does not encode an amino acid sequence, to essentially identical sequences. One of skill will recognize that individual substitutions, deletions or additions which alter, add, or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variants" or "conservative variations" of a listed polypeptide sequence of the present invention include substitutions of a small percentage, typically less than 5%, more typically less than 2% or 1%, of the amino acids of the polypeptide sequence with an amino acid of the same conservative substitution group. The addition of sequences that do not alter the encoded activity of a nucleic acid molecule, such as the addition of a non-functional sequence, is a conservative variation of the basic nucleic acid.

Conservative substitutions providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule.

Comparative hybridization can be used to identify nucleic acids of the invention, such as those in the sequence listing herein, including conservative variations of nucleic acids of the invention, and this comparative hybridization method is a one method of distinguishing nucleic acids of the invention from unrelated nucleic acids. In addition, target nucleic acids that hybridize to a nucleic acid represented by those of the sequence listing under high, ultra-high, and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 2% as well to the probe as to the perfectly matched complementary target, i.e., with a signal to noise ratio at least 95% as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking, and the like. An extensive guide to the hybridization of nucleic acids is found in Tijssen, *Laboratory Techniques in Biochemistry and Molecular Biology—Hybridization with Nucleic Acid Probes* (part I, chapter 2), *Overview of principles of hybridization and the strategy of nucleic acid probe assays*, Elsevier, N.Y. (1993); Hames and Higgins, *Gene Probes* 1 *and* 2 IRL Press at Oxford University Press, Oxford, England (1995). Several art-recognized methods are available for the synthesis, labeling, detection, and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes. Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration or increasing the concentration of organic solvents such as formalin in the hybridization or wash) until a selected set of criteria are met.

For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point (Tm) for a particular probe. The Tm is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the Tm for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least 2% that of the perfectly matched complementary target nucleic acid is said to bind to the probe under ultra-high stringency conditions.

Similarly, even higher levels of stringency can be determined by gradually increasing the hybridization or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least half that of the perfectly matched complementary target nucleic acid is said to bind to the probe under ultra-ultra-high stringency conditions.

Nucleic acids that do not hybridize to each other under stringent conditions are still substantially identical if the polypeptides that they encode are substantially identical. This occurs, e.g., when a copy of a nucleic acid is created using the maximum codon degeneracy permitted by the genetic code.

DNA sequences generated by sequencing reactions may contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence, for example, one base insertion or deletion in an open reading frame of over 1000 bases. Notwithstanding any errors in the sequence data disclosed herein, the principles of the invention will nevertheless be readily comprehended by one skilled in the art.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence shown in the appended sequence listing, or fragments thereof, will encode polypeptides "having synthetase functional activity". In fact, because degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having synthetase functional activity. This is because the skilled artisan is fully aware of amino acid substitutions that are either less likely or not likely to significantly effect protein function (e.g., replacing one aliphatic amino acid with a second aliphatic amino acid).

The terms "identical" or percent "identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms available to persons of skill or by visual inspection.

The phrase "substantially identical", in the context of two nucleic acids or polypeptides (e.g., DNAs encoding an O-tRNA or O—RS, or the amino acid sequence of an O—RS) refers to two or more sequences or subsequences that have at least about 60%, about 80%, about 90-95%, about 98%, or about 99%, or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

For sequence comparison and percent identity determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) to the reference sequence, based on the designated program parameters.

Optimal alignment of sequences for comparison can be conducted, e.g., by the local homology algorithm of Smith and Waterman, Adv. Appl. Math. 2, 482 (1981), by the homology alignment algorithm of Needleman and Wunsch, Mol. Biol. 48, 443 (1970), by the search for similarity method of Pearson and Lipman, Proc. Natl. Acad. Sci. U.S.A. 85, 2444 (1988), by computerized implementations of these algorithms (GAP, BESTFIT, FASTA, and TFASTA in the Wisconsin Genetics Software Package, Genetics Computer Group, Madison, Wis., USA), or by visual inspection.

One example of an algorithm that is suitable for determining percent sequence identity and sequence similarity is the BLAST algorithm, which is described in Altschul, et al., J. Mol. Biol. 215, 403-10 (1990). Software for performing BLAST analyses is publicly available through the National Center for Biotechnology Information (on the world wide web at ncbi.nlm.nih.gov). See, Henikoff and Henikoff, Proc. Natl. Acad. Sci. U.S.A. 89, 10915 (1989). In addition to calculating percent sequence identity, the BLAST algorithm also performs a statistical analysis of the similarity between two sequences. See, e.g., Karlin and Altschul, Proc. Natl. Acad. Sci. U.S.A. 90, 5873-787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

As used herein, the term "amino acid" refers to an organic acid containing both a basic amino group ($NH_2$) and an acidic carboxyl group ($CO_2H$). Naturally occurring amino acids are α-amino acids of the general formula ($NH_2$)($CO_2H$)CHR, where R group is different for each amino acid. Naturally occurring amino acids include selenocysteine or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. See, e.g., Stryer, Biochemistry, 3rd ed., Freeman and Company, New York (1988). Fluorinated amino acids are unnatural amino acids. Several fluorinated amino acids are commercially available, e.g., from Sigma Aldrich (Milwaukee, USA). Still other novel fluorinated amino acids are disclosed herein. Those that are not commercially available are optionally synthesized using standard methods known to those of skill in the art.

Unnatural amino acid uptake by a cell is one issue that is typically considered when designing and selecting fluorinated amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done that assesses which unnatural amino acids, if any, are taken up by cells. See, e.g., Liu, et al., *Progress toward the evolution of an organism with an expanded genetic code*, Proc. Natl. Acad. Sci. U.S.A. 96, 4780-85 (1999). Fluorinated amino acids for use according to the invention may exist in different stereoisomeric forms by virtue of the presence of asymmetric centers in the compounds; i.e., each asymmetric carbon may have either the R- or S-configuration. All such stereoisomeric forms, as well as mixtures thereof, including racemic mixtures, form part of this invention. In an advantageous embodiment of the invention, a racemic fluorinated amino acid may be used where the translation system discriminates between enantionmers.

The fluorinated amino acid can be essentially any suitable fluorine-containing amino acid, e.g., one whose introduction is not predicted to significantly perturb the protein's structure. Fluorinated amino acids for use in the invention include compounds fluorinated aromatic amino acids, such as fluorinated phenylananine, fluorinated p-methylphenylalanine, or fluorinated p-benzoylphenylalanine, wherein at least one carbon atom of the fluorinated amino acid is substituted with a fluorine atom or a fluorine-substituted lower alkyl group, such as a trifluoromethyl group. The fluorinated amino acid should comprise at least one fluorine atom, such as a $^{19}F$ atom or a $^{18}F$ atom. The fluorinated amino acid may also comprise a photocrosslinking moiety or a photolabile group. Also disclosed herein are heretofore unknown fluorinated amino acids, which may be used in the methods of the invention.

A preferred amino acid for use in the methods of the invention is trifluoromethyl-phenylalanine (tfmPhe), particularly para-trifluoromethyl-L-phenylalanine. In addition, other fluorinated amino acid analogs that may be used in the methods of the invention include bioisosteres of tyrosine. Bioisosterism is a well-known tool for predicting the biological activity of compounds, based upon the premise that compounds with similar size, shape, and electron density can have similar biological activity. To form a bioisostere of a given molecule, one replaces one or more atoms or groups with known bioisosteric replacements for that atom or group. Known bioisosteric replacements include, for example, the interchangeability of —F, —OH, —$NH_2$, —Cl, and —$CH_3$; the interchangeability of —Br and -iso-$C_3H_7$; the interchangeability of —I and -tert-$C_4H_9$; the interchangeability of —O—, —S—, —NH—, —$CH_2$—, and —Se—; the interchangeability of —N=, —CH=, and —P=; the interchangeability of phenyl and pyridyl groups; the interchangeability of —C=C— and —S— (for example, benzene and thiophene); the interchangeability of an aromatic nitrogen ($R^1$—N($R^3$)—$R^2$) for an unsaturated carbon ($R^1$—C(=$R^3$)—$R^2$); and the interchangeability of —CO—, —SO—, and —$SO_2$—. These examples are not limiting on the range of bioisosteric equivalents and one of skill in the art will be able to identify other bioisosteric replacements known in the art.

Further examples of fluorinated amino acids of the invention include compounds according to the following formula:

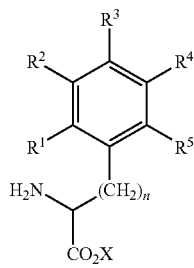

wherein n=0, 1, 2, or 3; X is $H^+$ or a biologically compatible cationic group; and $R^1$, $R^2$, $R^3$, $R^4$, and $R^5$ are selected from the group consisting of hydrogen, fluorine, lower alkyl groups, and fluorine-substituted lower alkyl groups, wherein the compound comprises at least one fluorine atom.

The term "lower alkyl" means a straight or branched chain hydrocarbon group having six or fewer carbon atoms. Representative examples of lower alkyl groups include methyl, ethyl, propyl, isopropyl, isobutyl, butyl, tert-butyl, sec-butyl, pentyl, and hexyl groups. An example "fluorine-substituted lower alkyl group" is a trifluoromethyl group.

Representative "biologically compatible cationic groups" include cations based on the alkali and alkaline earth metals, such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like.

Still further examples of fluorinated amino acids of the invention include compounds according to the following formula:

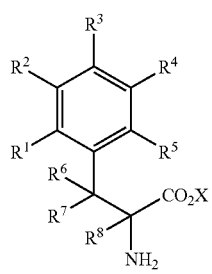

wherein X is $H^+$ or a biologically compatible cationic group; and $R^1$, $R^2$, $R^3$, $R^4$, $R^5$, $R^6$, $R^7$, and $R^8$ are selected from the group consisting of hydrogen, fluorine, lower alkyl groups, and fluorine-substituted lower alkyl groups, wherein the compound comprises at least one fluorine atom.

Further examples of fluorinated amino acids of the invention include compounds according to either of the following formulae:

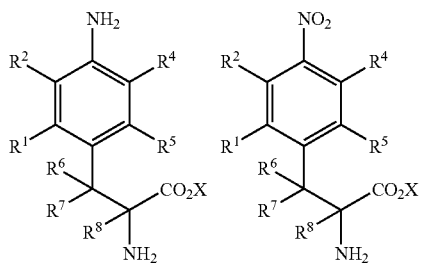

wherein X is $H^+$ or a biologically compatible cationic group; and $R^1$, $R^2$, $R^4$, $R^5$, $R^6$, $R^7$, and $R^8$ are selected from the group consisting of hydrogen, fluorine, lower alkyl groups, and fluorine-substituted lower alkyl groups, wherein the compound comprises at least one fluorine atom. These amino- and nitro-substituted compounds are of particular interest because after they have been incorporated into a protein they may be further synthetically modified.

Still further examples of fluorinated amino acids of the invention include compounds according to the following formula:

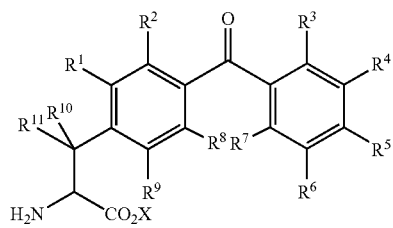

wherein X is $H^+$ or a biologically compatible cationic group; and $R^1$, $R^2$, $R^3$, $R^4$, $R^5$, $R^6$, $R^7$, $R^8$, $R^9$, $R^{10}$, and $R^{11}$ are selected from the group consisting of hydrogen, fluorine, lower alkyl groups, and fluorine-substituted lower alkyl groups, wherein the compound comprises at least one fluorine atom. These benzophenone compounds are of particular interest because after they have been incorporated into a protein they may be modified by photo crosslinking.

Additional examples of fluorinated amino acids of the invention include compounds according to one of the following formulae:

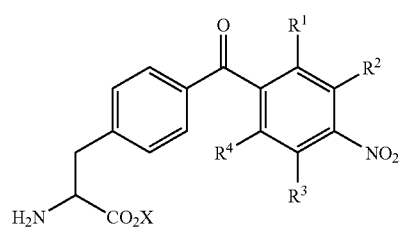

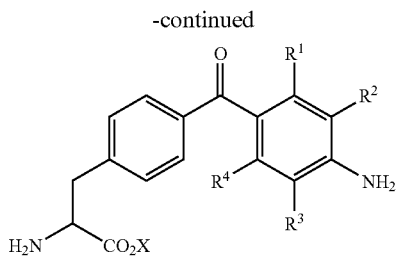
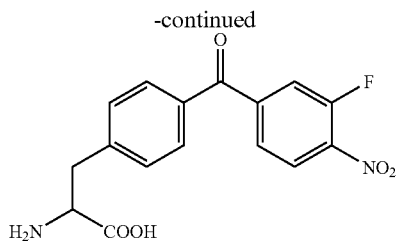

wherein X is H+ or a biologically compatible cationic group; and R¹, R², R³, and R⁴ are selected from the group consisting of hydrogen, fluorine, lower alkyl groups, and fluorine-substituted lower alkyl groups, wherein the compound comprises at least one fluorine atom. These amino- and nitro-substituted compounds are of particular interest because after they have been incorporated into a protein they may be further synthetically modified.

Other specific examples of fluorinated amino acids of the invention include the following compounds, as well as their biologically compatible salts:

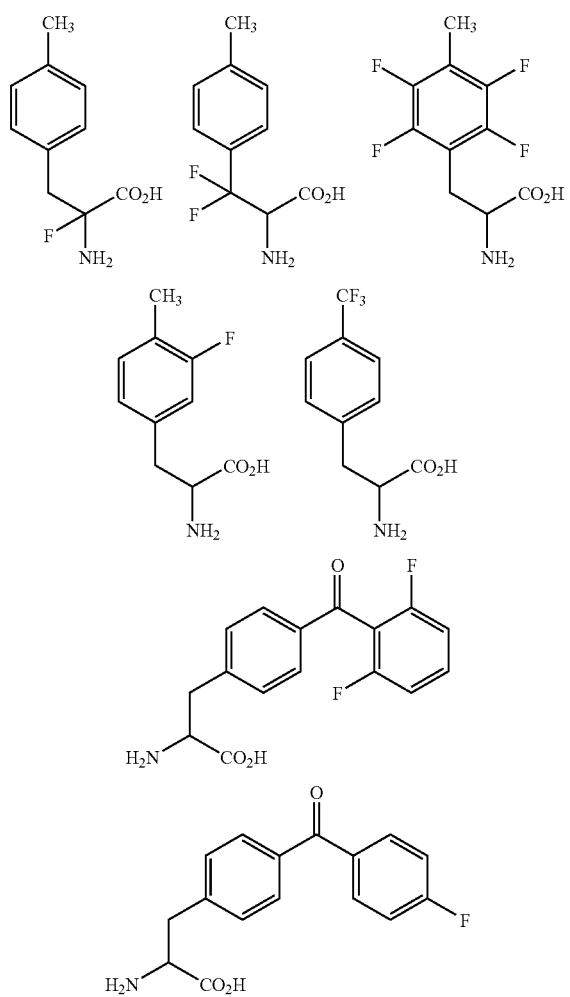

Methods of producing a protein in a cell (e.g., a non-eukaryotic cell, such as an *E. coli* cell or the like, or a eukaryotic cell) with a fluorinated amino acid at a specified position are a feature of the invention. Proteins or polypeptides of interest having at least one fluorinated amino acid are a feature of the invention. Optionally, a protein of the invention may include a post-translational modification. In certain embodiments, the protein comprises an amino acid sequence that is at least 75% identical to that of a known protein, e.g., a therapeutic protein, a diagnostic protein, an industrial enzyme, or portion thereof.

Essentially any protein (or portion thereof) that includes a fluorinated amino acid, or that encodes multiple different unnatural amino acids (and any corresponding coding nucleic acid, e.g., which includes one or more selector codons) can be produced using the compositions and methods herein. No attempt is made to identify the hundreds of thousands of known proteins, any of which may be modified to include one or more unnatural amino acid, e.g., by tailoring any available mutation methods to include one or more appropriate selector codon in a relevant translation system. Common sequence repositories for known proteins include GenBank, EMBL, DDBJ, and the NCBI, among others. Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Essentially any protein whose structure is of interest can be modified to include a fluorinated amino acid.

Enzymes (e.g., industrial enzymes) or portions thereof with at least one fluorinated amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

To make a protein that includes a fluorinated amino acid, one may use host cells and organisms that are adapted for the in vivo incorporation of the fluorinated amino acid via orthogonal tRNA/RS pairs. Host cells are genetically engineered (e.g., transformed, transduced, or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

The compositions of the invention and compositions made by the methods of the invention are optionally made in a cell. The O-tRNA/O—RS pairs or individual components of the invention may then be used in a host system's translation machinery, which results in a fluorinated amino acid being incorporated into a protein. For example, when an O-tRNA/O—RS pair is introduced into a host, e.g., *Escherichia coli*, the pair leads to the in vivo incorporation of a fluorinated amino acid, which can be exogenously added to the growth medium, into a protein, e.g., any protein whose structure is of interest, in response to a selector codon, e.g., an amber nonsense codon. Optionally, the compositions of the invention can be in an in vitro translation system, or in an in vivo system(s) with the fluorinated amino acid and may be used to facilitate studies on protein structure, function, and the like.

Kits are also a feature of the invention. For example, a kit for producing a protein with a fluorinated amino acid at a specified position is provided, where the kit includes a cell comprising an orthogonal tRNA that functions in the cell and recognizes a selector codon and an orthogonal aminoacyl-tRNA synthetase, packaged in one or more containers. For example, the O—RS may comprise an amino acid sequence of SEQ ID NO:3 or a conservative variant thereof. In one class of embodiments, the kit further includes a fluorinated amino acid. In another class of embodiments, the kit further comprises instructional materials for producing the protein, an appropriate cell growth medium, reagents for introducing a target nucleic acid encoding the protein of interest and including the selector codon into the cell, or the like. Any composition, system or device of the invention can also be associated with appropriate packaging materials (e.g., containers, etc.) for production in kit form. A kit may also include a plasmid and instructions for practicing a method of the invention.

Site-specific, efficient incorporation of fluorinated amino acids into proteins facilitates solution of protein structures by NMR spectroscopy. Fluorine atom incorporation using the methods and compositions of the invention can be used to facilitate determination of the structure of essentially any protein, but can be particularly advantageous for proteins that are not readily crystallized. A protein including the fluorinated amino acid may be isolated and the structure of the protein is determined by nuclear magnetic resonance (NMR) spectroscopy.

The invention also relates to methods of characterizing the structure, dynamics, and reactivity of proteins ex vivo by NMR. Proteins are typically purified prior to NMR analysis, e.g., from natural sources, from an in vitro translation system, from cells (e.g., bacteria, yeast, etc.) overexpressing a protein of interest by any of a number of methods well known in the art, including, e.g., ammonium sulfate or ethanol precipitation, centrifugation, acid or base extraction, column chromatography, affinity column chromatography, anion or cation exchange chromatography, phosphocellulose chromatography, high performance liquid chromatography (HPLC), gel filtration, hydrophobic interaction chromatography, hydroxylapatite chromatography, lectin chromatography, gel electrophoresis, and the like. In addition to other references noted herein, a variety of protein purification methods are well known in the art.

The present invention also includes screening methods for use in structure activity relationship and drug discovery applications. "Structure-activity relationship (SAR)" refers to the way in which altering the molecular structure of drugs alters their interaction with a protein, receptor, enzyme, etc. For example, the interaction of a fluorinated protein with one or more drug candidates may be monitored by $^{19}$F-NMR. In one embodiment, a fluorinated protein is mixed with multiple drug candidates and the mixture is analyzed by NMR using art-recognized methods to determine the relative affinity of the components of the mixture for the protein.

In another embodiment, the dynamics of a ligand-protein interaction may be followed by $^{19}$F-NMR as illustrated in the Examples. See, Gerig, Magnetic Resonance in Chemistry 37, 647-52 (1999). In yet another embodiment of the invention, the dymanic solution-phase behavior of a protein may be studied by $^{19}$F-NMR. Incorporation of fluorine into a protein in some circumstances causes a protein to be more stable in solution, and the present invention may be applied to the study of such stabilized proteins. The invention therefore facilitates the study of protein solution-phase structures. The invention is especially advantageously applied to the study of proteins that are not easily crystallized, and therefore are not amenable structural analysis by X-ray crystallography. In another embodiment, the invention is especially useful in the NMR study of proteins larger than about 30 kDa. Conventional NMR methods are not able to resolve individual signals of hydrogen or carbon nuclei for very large proteins. Because the invention permits the selective incorporation of fluorine into proteins and because such proteins have a limited number of NMR fluorine signals, the invention permits the study of large proteins by NMR.

The methods of the present invention also include the synthesis and administration of fluorine-containing proteins for medical diagnosis, such as magnetic resonance imaging and positron emission tomography. Magnetic resonance imaging (MRI) of tissue water can be used to measure perfusion and diffusion with submillimeter resolution. Magnetic resonance spectroscopy may be applied to the assessment of tissue metabolites that contain protons, phosphorus, fluorine, or other nuclei. The combination of imaging and spectroscopy technologies has lead to spectroscopic imaging techniques that are capable of mapping proton metabolites at resolutions as small as 0.25 cm$^3$. Zakian, et al., Semin. Radiat. Oncol. 11, 3-15 (2001). Molecular MR imaging employs contrast agents bound to targeting molecules that illuminate specific cell types or sub-organ structures. Molecular imaging has been successfully used to monitor angiogenesis and inflammation based on unique surface molecules expressed in growing vascular tissue and in cells of the immune system. Singh, et al., Adv. Drug Del. Reviews 41, 7-20 (2000). In magnetic resonance angiography (MRA) contrast agents are used to image the arteries and veins for diagnosing cardiovascular disease and associated disorders.

Fluorinated proteins are of considerable interest for $^{19}$F-MRI studies due to the attractive features of $^{19}$F as an in vivo probe. The sensitivity of $^{19}$F is very high, approximately 83% as sensitive as protons. Little or no background $^{19}$F MR signal arises from fluorine of biological origin, and $^{19}$F MR signals are only from exogenously administered materials. In some applications $^{19}$F-MRI is superior to $^1$H-MRI techniques. $^{19}$F has essentially no background signal, whereas $^1$H background arises from abundant water in biological tissues. Furthermore, because the observed signal intensity directly correlates with $^{19}$F spin densities, $^{19}$F MRI permits quantitation of administered $^{19}$F probe. Of particular interest is fluorine's diagnostic value in non-invasive imaging applications. $^{19}$F MRI can therefore be used to monitor biological activity in medical applications. See, e.g., Mehta, et al., Bioconjugate Chem. 5, 257-61 (1994); Higuchi, et al., Nature Neurosci. 8, 527-533 (2005); Ulrich, Prog. Nuclear Magnetic Resonance Spec. 46, 1-21 (2005).

The invention also relates to $^{18}$F imaging with positron emission tomography (PET). Positrons are positively charged electrons (anti-electrons) that are emitted by radionuclides, usually prepared using a cyclotron or other device. Radionuclides such as $^{18}$F are often employed as radioactive tracers in radiopharmaceuticals, for example by incorporating them into substances such as glucose, used in the medical imaging field. Typically, a radiopharmaceutical is injected into a patient and accumulates in an organ that is to be imaged. It is known that specific radiopharmaceuticals become concentrated within certain organs. The process of concentrating often involves metabolic processes such as glucose and fatty acid metabolism, cellular uptake, and protein synthesis. After a radiopharmaceutical becomes concentrated within an organ of interest and while the radionuclides decay, positrons are emitted. The positrons travel a very short distance before they encounter an electron and, when the positron encounters an electron, the positron is annihilated and converted into two photons, which are used to generate an image. See, e.g., Shimizu, et al., Magnetic Resonance in Medicine 5, 290-95 (1987); Vaalburg, et al., Nucl. Med. Biol. 19, 227-37 (1992).

Radiopharmaceuticals typically should be stereochemically pure in order to ensure that an organ of interest efficiently accumulates the radiopharmaceutical and that the background signal is minimized. Similar considerations apply to MRI. In certain applications, the translation system of the present invention may employ a racemic mixture of fluorinated amino acids. In such cases, the cell selects the appropriate stereoisomer and racemizes other stereoisomers prior to protein synthesis. For example, a mixture of D,L-fluorinated amino acids may be used ex vivo to fluorine-label a protein prior to administration to a patient, the resulting fluorinated protein comprising substantially only L-fluorinated amino acid.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. One of skill in the art will appreciate that the invention is not limited to those exact sequences, e.g., as in the Examples and sequence listing. One of skill will appreciate that the invention also provides, e.g., many related and unrelated sequences with the functions described herein, e.g., encoding an appropriate O-tRNA or an O—RS. The invention is further illustrated by the foregoing examples, which should not be construed as further limiting.

EXAMPLES

In an exemplary embodiment, protein interface and active site changes resulting from inhibitor binding and redox changes in the cancer prodrug activator, nitroreductase, were studied by selective introduction of trifluoromethyl-L-phenylalanine (tfmPhe) and subsequent monitoring of the three NMR equivalent atoms. TfmPhe gives a strong single $^{19}$F NMR signal resulting from a single rigid CF$_3$ group, and it has been reported to functionally replace certain amino acids, such as phenylalanine and tyrosine, depending on the protein structure. Ulrich, *Solid State $^{19}$F NMR Methods for Studying Biomembranes*, Progress in Nuclear Magnetic Resonance Spectroscopy 46, 1-21 (2005).

The preparation of a new *M. jannaschii* TyrRS (MjTyrRS) that specifically incorporates tfmPhe into proteins in response to a TAG stop codon in *E. coli* was confirmed by SDS-PAGE analysis of tfmPhe incorporation into NTR-124 as compared to native NTR (nitroreductase) and NTR-124 suppression with original MjTyrRS/tRNA$^{Tyr}{}_{CUA}$. In a silver-stained gel of NTR samples purified by immobilized metal affinity chromatography, no NTR was detectable by silver stain after SDS-PAGE when tfmPhe was withheld. These studies describe the first site-specific in vivo incorporation of a fluorinated amino acid. The tfmPhe was incorporated into *E. coli* NTR with high yield and was used to monitor small molecule binding and protein conformational changes. The tfmPhe protein shows strong sharp $^{19}$F NMR signals for in vivo and in vitro studies with the standard advantages of environmentally sensitive chemical shifts. The high fidelity labeling resulting from this method also allows access to in vivo experiments and quantification of protein conformational states. Because tfmPhe is incorporated genetically, any protein that is expressed in *E. coli*, irrespective of size or sequence, can be studied using this technique. The ease with which labeled proteins can be produced facilitates the study of protein conformations, interactions, and processing.

To demonstrate the utility of the $^{19}$F signal from tfmPhe in probing protein conformational changes by NMR, tfmPhe was incorporated into the interface of *E. coli* nitroreductase (NTR) at two interface locations: the dynamic active site residue F124, and stationary Y36 residue. Lovering, et al., *The Structure of Escherichia coli Nitroreductase Complexed with Nicotinic Acid: Three Crystal Forms at 1.7 Å, 1.8 Å and 2.4 Å Resolution*, J. Mol. Biol. 309(1), 203-13 (2001); Haynes, et al., *Structures of Nitroreductase in Three States: Effects of Inhibitor Binding and Reduction*, J. Biol. Chem. 277(13), 11513-20 (2002). NTR is a homodimeric, 48 kDa nonspecific nitroreductase that uses a bound flavin mononucleotide (FMN) in two symmetrically placed interface active sites. NTR uses NADH or NADPH in a ping-pong, bi-bi mechanism to reduce a broad range of substrates. The structure, mechanism, and optimization of NTR have been studied extensively because it is currently in clinical trials to activate nitroaryl prodrugs for gene-directed cancer therapy. Hu, et al., *Nitroaryl Phosphoramides as Novel Prodrugs for E. coli Nitroreductase Activation in Enzyme Prodrug Therapy*, J. Med. Chem. 46(23), 4818-21 (2003); Grove, et al., *Generation of Escherichia coli Nitroreductase Mutants Conferring Improved Cell Sensitization to The Prodrug CB1954*, Cancer Res, 63(17), 5532-37 (2003). Crystal structures of NTR have shown Phe-124 moving in order to bind nicotinic acid (a competitive inhibitor of NADH), while no movement is detected at the nearby interfacial Tyr-36 site. Currently there have been no reported structures of *E. coli* NTR in the reduced form, the form actually binding the electron-receiving substrate. The oxidized and reduced crystal structures of homologous (88% identity) *E. cloacae* NTR show no detectable effect at Tyr-36, while the movement of Phe-124 is comparable to that produced when nicotinic acid binds in the *E. coli* structure. Because the FMN's bound at the interface could significantly perturb the protein interface and active sites, tfmPhe incorporated at Phe-124 and Tyr-36 reports structural changes due to ligand binding and redox state via changes in $^{19}$F NMR chemical shift.

The in vivo, high fidelity incorporation of tfmPhe into proteins is accomplished by modifying a *Methanococcus jannaschii* suppressor tRNA/aminoacyl-tRNA synthetase pair (MjTyrRS/tRNA$^{Tyr}{}_{CUA}$). The orthogonality of the MjTyrRS/tRNA$^{Tyr}{}_{CUA}$ with all the *E. coli* synthetase/tRNA pairs ensures there is no background incorporation of tfmPhe into any other amino acid sites and that incorporation into the desired TAG site approaches natural fidelity levels. Xie, et al., *The Site-Specific Incorporation of p-Iodo-L-Phenylalanine into Proteins for Structure Determination*, Nat. Biotechnol. 22(10), 1297-1301 (2004). In order to generate a MjTyrRS that is selective for tfmPhe, a 6×10$^7$ library of MjTyrRS mutants in which six residues were randomized was studied. See, e.g, WO 2005/116237; WO 2005/038002; WO 2002/

086075; and WO 2002/085923. The mutant library was passed through three rounds of alternating positive and negative selection. Xie, et al., *An Expanding Genetic Code*, Methods 36(3), 227-38 (2005); Mehl, et al., *Generation of A Bacterium with A 21 Amino Acid Genetic Code*, J. Am. Chem. Soc. 125(4), 935-39 (2003). By challenging the cells to grow in the presence and absence of tfmPhe in the positive and negative selections, respectively, only mutants expressing synthetases that efficiently incorporate tfmPhe in response to the TAG codon survive.

The two top performing synthetases were subcloned into the pDule vector (pDule-tfmPhe1 and pDule-tfmPhe2) for further analysis of a protein containing tfmPhe. The medium copy pDule plasmid is designed to contain both the tRNA$^{Tyr}_{CUA}$ and new synthetase allowing a standard high copy protein expression plasmid for use in production of tfmPhe containing protein. Full length NTR was produced when cells containing both plasmids pDule-tfmPhe1 (tfmPheRS/tRNA$^{Tyr}_{CUA}$) and pTrc-NTR-124TAG (nitroreductase with TAG codon at Phe124) were induced to produce protein in modified minimal media supplemented with tfmPhe. Farrell, et al., *Photo-Cross-Linking Interacting Proteins with A Genetically Encoded Benzophenone*, Nat. Methods 2(5), 377-84 (2005). Both new tfmPhe synthetases functioned equally well and pDule-tfmPhe1 was arbitrarily chosen for characterization and NMR studies. The purified yield of NTR-tfmPhe-124 ranged from 12-24 mg/L and NTR-tfmPhe-36 from 10-16 mg/L, while positive controls native NTR and NTR-Tyr-124 from the original MjTyrRS yielded 17-30 mg/L and 7-12 mg/L, respectively.

Native NTR and NTR-tfmPhe-124 were analyzed by electrospray-ionization quadrupole time-of-fight mass spectrometry (ESI-Q-Tof Ultima) to further demonstrate that only a single tfmPhe is inserted in response to the TAG codon. The native NTR and NTR-tfmPhe-124 showed the calculated mass shift of 68 Da, having masses 27674.1±0.2 Da and 27742.9±0.4 Da, respectively. To verify that the discrete incorporation of tfmPhe for Phe only takes place at site 124, isolated proteins were digested by trypsin and the fragments were analyzed by mass spectrometry (Micromass Q-T of). The only peptide fragment containing tfmPhe was the expected F(tfmPhe)ADMHR fragment or (tfmPhe)ADMHR fragment with 96.2% confidence and >80% coverage. No masses were observed in the mass spectra corresponding to natural amino acid incorporation at site 124. These results confirm the high fidelity and efficiency of tfmPhe incorporation into proteins.

To confirm that incorporating tfmPhe had minimal structural effect on NTR, native NTR activity and $K_I$ values of the competitive nicotinic acid were compared to those for NTR-tfmPhe-124 and NTR-tfmPhe-36 by monitoring the consumption of NADH when reducing menadione. Native NTR activity and $K_I$ are $7.7 \times 10^5$ M$^{-1}$s$^{-1}$ and 20 mM respectively, while NTR-tfmPhe-124 was 6.5% more active with a $K_I$ of 21 mM and NTR-tfm-36 was 27% less active with a $K_I$ of 78 mM. The alteration of these sites has little effect on NTR activity, and therefore tfmPhe is a reasonable structural mimic for Tyr and Phe.

Figure 2:
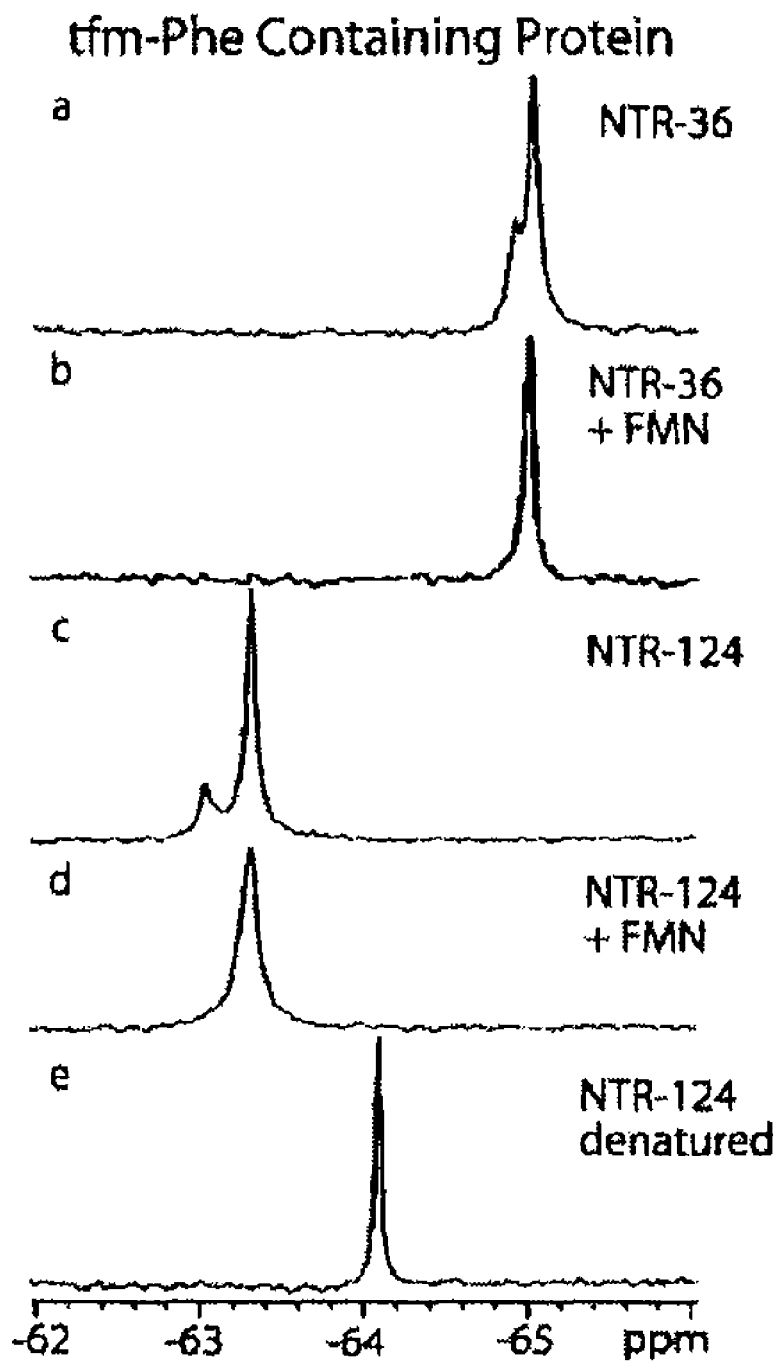
FIG. 2 shows the $^{19}F$ NMR spectra of a protein containing tfmPhe. Spectra are referenced to an internal standard of 4-fluorotoluene in toluene-$d_8$ at −120.771 ppm.

In all tfmPhe labeled proteins studies thus far, the CF$_3$ group has been free to rotate on NMR timescales resulting in a sharp single peak, and spectra containing anything but a single peak have been a result of multiple protein conformations. While well-resolved spectra have been acquired for tfmPhe-containing proteins in under 2 min. using a $^{19}$F NMR probe, all spectra presented here were collected between 1 and 18 hrs on a standard broad band probe with the proton coil tuned to the $^{19}$F frequency. As expected, totally solvent exposed tfmPhe-peptides, like those of denatured protein, show a narrow chemical shift range (−64.1 to −64.4 ppm) while even slightly more internalized sites shift appreciably (FIG. 2). The left shoulder on NTR-tfmPhe-36 and NTR-tfmPhe-124 is due to pure protein devoid of bound FMN that collapses to a single peak by prolonged incubation with FMN (FIG. 2*a-d*).

Figure 3:
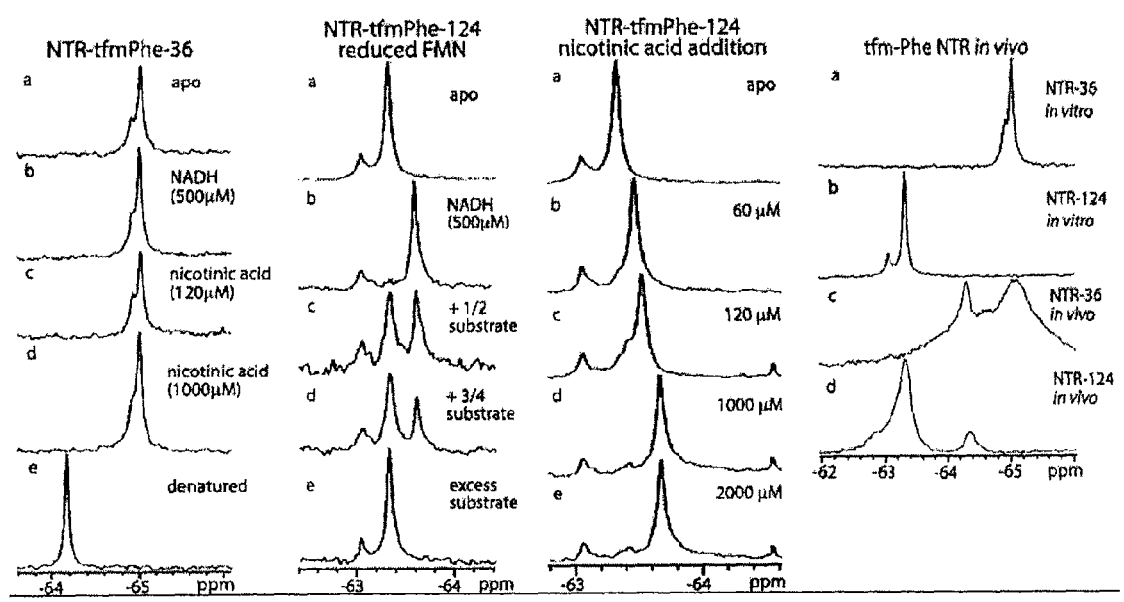
FIG. 3 depicts the in vitro $^{19}F$ NMR spectra of NTR-tfmPhe-36 and NTR-tfmPhe-124 with the addition of an inhibitor and substrates. Column one shows the effect of active site binding and unfolding on NTR-tfmPhe-36 protein. Column two (a, b) shows the affects of reducing the active site FMN (flavin mononucleotide) in NTR-tfmPhe-124 by addition of excess NADH (reduced nicotinamide adenine dinucleotide). Stepwise reoxidation of NTR-tfmPhe-124 is shown by addition of menadione (c-e). Column three shows the stepwise addition of nicotinic acid to NTR-tfmPhe-124. The fraction of NTR-tfmPhe-124 without bound FMN is unaffected by active site binding (peak at −63.04 ppm) or denatured protein (peak at −64.56 ppm). Column four shows comparison of in vivo vs. in vitro $^{19}F$ spectra for NTR-tfmPhe protein. The peak at −64.3 ppm in both in vivo (c, d) spectra likely represent residual free tfmPhe in the cell or denatured protein. While buffered free tfmPhe $^{19}F$ signal is at −64.65 ppm, addition of free amino acid to in vivo samples increased the −64.3 ppm signal.

As predicted by crystal structures, NTR-tfmPhe-36 is not affected by the addition of inhibitor concentrations well above the protein's $K_I$ or by reduction (FIG. 3, column 1). In contrast to NTR-tfmPhe-36, the signal from NTR-tfmPhe-124 is very sensitive to conformational changes in the active site. The reduction of FMN in NTR-tfmPhe-124 causes an upfield shift from −63.32 to −63.60 ppm (FIG. 3, column 2). Since this conformational change involves a tightly bound cofactor, one is able to monitor separate peaks as protein is oxidized by stepwise addition of substrate. NTR-tfmPhe-124 signal is also affected by nicotinic acid binding as predicted by crystal structures (FIG. 3, column 3).

Figure 4:
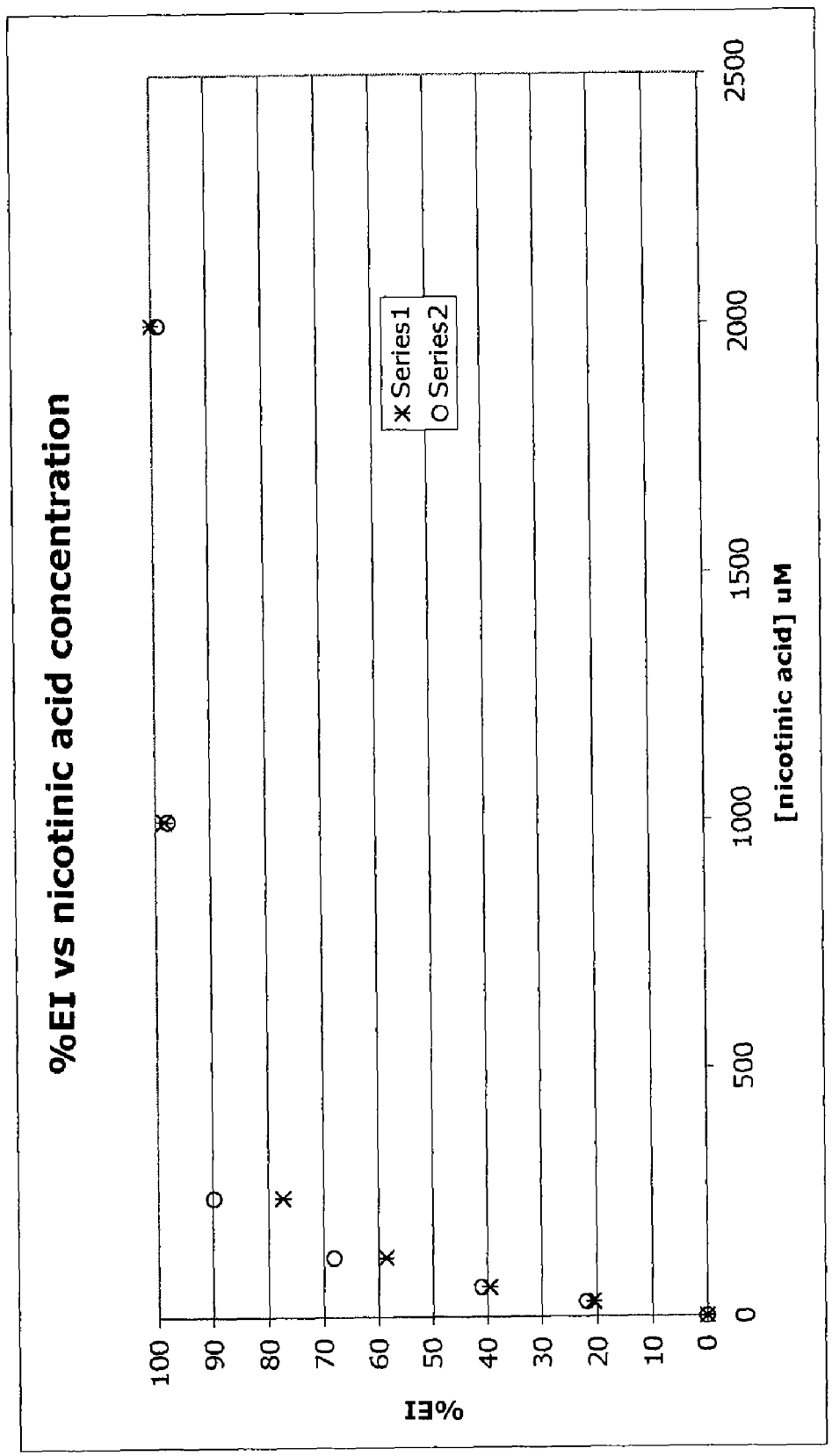
FIG. 4 is a comparison of theoretical % ES (enzyme-substrate) complex in solution to % ES complex predicted from NMR shift. Series 2 is theoretical % ES based on experimental starting enzyme concentration and $K_I$. Series 1 is the percentage that the peak has shifted to fully bound complex, assuming 2000 mM nicotinic acid to be 100% EI (enzyme-inhibitor) complex. Theoretical % ES (Series 2) is calculated using the standard equation for competitive inhibition, $K_I$= (enzyme conc.)(inhibitor conc.)/(enzyme inhibitor complex conc.). The $K_I$ of NTR-tfmPhe-124 was determined experimentally to be 21.3 mM. The enzyme concentration was determined to be 110 mM. The initial inhibitor concentrations were 30 mM, 60 mM, 120 mM, 240 mM, 1000 mM, and 2000 mM. % EI was calculated for each inhibitor concentration and plotted against the initial inhibitor concentration for Series 2. NMR calculated % ES (Series 1) was determined by assuming that no addition of inhibitor resulted in a chemical shift representing 0% ES, whereas 2000 mM nicotinic acid represented a chemical shift for 100% ES. Using these chemical shifts as 0% and 100% endpoints, chemical shift difference that resulted from adding nicotinic acid was plotted against the added inhibitor concentrations for Series 1. Any discrepancies in these curves may result from errors in protein concentration or experimentally determined $K_I$.

In contrast to NTR reduction, a single exchange-average resonance is observed due to the rapid interconversion rate of nicotinic acid-bound and unbound NTR forms relative to the NMR frequency difference for these forms. Because nicotinic acid is a competitive inhibitor for the oxidized form of NTR, the displacement of this average signal from apo-NTR should represent the amount of enzyme-inhibitor complex in solution. The normalized $^{19}$F signal shift matches well with % ES complex calculated from $K_I$=E*I/EI (FIG. 4). The lack of change in $^{19}$F NMR signal for NTR-tfmPhe-36 and similarity of signal shift for NTR-tfmPhe-124 indicate that the minimal interface conformational changes in *E. coli* NTR from reducing FMN and binding nicotinic acid match that of *E. cloacae* NTR.

Labeled NTR was also monitored in vivo. While the signal quality of tfmPhe is sufficient to resolve NTR-tfmPhe-36 and NTR-tfmPhe-124 from each other in vivo, monitoring protein dynamics in vivo was not feasible due to the poor cell permeability of nicotinic acid and NADH (FIG. 3, column 4). Multiple attempts at preparing the NTR-tfmPhe-36 sample in order to reduce its large peak width were unsuccessful. The broader shape of this surface exposed residue is attributed to its ability to sample multiple environments inside the cell.

Selection of tfmPhe specific tRNA-aminoacyl synthetase. A library of tRNA-aminoacyl synthetases was encoded on a kanamycin (Kn) resistant plasmid, pBK-JM-Lib, under control of the constitutive *E. coli* GlnRS promoter and terminator. The library was transformed by electroporation into DH10B *E. coli* containing the tetracycline (Tet) resistant positive selection plasmid, pREP2/YC-JYCUA. The positive selection plasmid encodes a mutant tRNA$^{Tyr}_{CUA}$, an amber disrupted chloramphenicol acetyltransferase, and an amber disrupted T7 RNA polymerase that drives the production of green fluorescent protein. The first positive selection was performed in the presence of 1 mM tfmPhe, 70 μg/mL chloramphenicol (Cm), 50 μg/mL Kn, and 25 μg/mL Tet in a modified GMML media at 37° C. with 250 rpm shaking until the OD was >1.0. Plasmid DNA was extracted and pBK-JM-Lib was separated from pREP2/YC-JYCUA by agarose gel electrophoresis. The purified pBK-JM-Lib was then transformed into DH10B *E. coli* containing the ampicillin (Amp) resistant negative selection plasmid, pJ17B3, encoding a mutant tRNA$^{Tyr}_{CUA}$, and an amber disrupted barnase gene under control of an arabinose promoter and rrnC terminator. The rescued negative selection cells were plated on Luria-Bertani (LB) agar plates containing 100 μg/mL Amp, 50 μg/mL Kn, and 0.2% arabinose. Following 18 hrs of growth at 37° C. the plates were scraped into LB media, plasmid DNA was extracted and pBK-JM-Lib was purified by gel electrophoresis. The remaining pBK-JM-Lib was transformed into positive selection cells and selected as described in modified GMML media but on agar plates instead of in liquid media. After two more rounds of positive and negative selection, remaining pBK-JM-Lib members were transformed into positive selection cells and grown on modified GMML media plates in the presence of 1 mM tfmPhe, 100 µg/mL Cm, 50 µg/mL Kn, 25 µg/mL Tet, and 0.002% arabinose. Single individual colonies (56) were selected from the surviving library and screened in this media in the presence and absence of tfmPhe and varying concentrations of Cm from 0 to 120 µg/mL. The efficiency and fidelity of the synthetases (7) that survived in greater than 120 µg/mL Cm with tfmPhe present and less than 10 µg/mL Cm in absence of tfmPhe were carried on to tfmPhe-protein production trials. The individual tfmPheRS plasmids were transformed into DH10B cells containing pBAD/JYAMB-4TAG (Tet resistance) that encodes the mutant tRNA$^{Tyr}_{CUA}$ and the amber disrupted sperm whale myoglobin gene. Mehl, et al., *Generation of A Bacterium with A 21 Amino Acid Genetic Code*, J. Am. Chem. Soc. 125(4), 935-39 (2003). The C-terminal His-6 tag on the protein facilitated monitoring of protein yield, as well as protein purity silver stained SDS-PAGE analysis. The two synthetases that produced the highest yield of purified tfmPhe-myoglobin when tfmPhe is added to the media were subcloned into the pDule vector under control of the 1pp promoter and the rrnB terminator. Farrell, et al., *Photo-Cross-Linking Interacting Proteins with A Genetically Encoded Benzophenone*, Nat. Methods 2(5), 377-84 (2005). These synthetases showed no detectable background myoglobin production when tfmPhe is withheld from the media. The resulting plasmids, pDule-tfmPhe1 and pDule-tfmPhe2, with their sequence changes (Y32L, L65A, F108S, H109H, D158A, and L162M) and (Y32Q, L65Q, F108Q, H109E, D158S, and L162A) respectively, performed equally well for incorporating tfmPhe into proteins, and pDule-tfmPhe1 was used for all further NMR and MS protein characterization.

Expression and purification of tfmPhe containing nitroreductase. The standard overexpression plasmid pTrcHisA containing the *E. coli* nitroreductase gene nfnB, had TAG mutations incorporated to replace P124 and T36 to create pTrc-NTR-124TAG and pTrc-NTR-36TAG. *E. coli* DH10B cells containing pDule-tfmPhe1 and pTrc-NTR-124TAG or pTrc-NTR-36TAG were grown in modified minimal media containing supplemented flavin at 10 µM and induced to produce protein with 1.0 mM IPTG at an OD of 0.8. See, e.g., Farrell, et al., *Photo-Cross-Linking Interacting Proteins with A Genetically Encoded Benzophenone*, Nat. Methods 2(5), 377-84 (2005). Cells were harvested 18 hrs after induction by centrifugation and stored at −80° C. Cells (from 0.5 L of media) for in vivo NMR measurements were thawed on ice, resuspended in 50 mL of PBS buffer (10 mM NaH$_2$PO$_4$, 140 mM NaCl pH 7.8) at 0° C., and repelleted by centrifugation at 5000 g. The cells for in vivo NMR spectra shown for NTR-tfmPhe-36 and NTR-tfmPhe-124 were washed 3 times and 5 times respectively. Protein for in vitro studies was purified to >95% by Co ion affinity chromatography using BD Talon resin. Pure protein was desalted into 10 mM tris-HCl buffer pH 7.8 using PD10 columns. Protein was concentrated by centrifugation to 3.0 mg/mL for NMR studies.

NMR data were collected using a Varian Unity INOVA 500 MHz spectrometer fitted with a 5 mm broadband probe. The proton coil was tuned to fluorine frequency (470.114 MHz). Standard decoupling parameters were used with a 100,000 Hz spectral width, 9 µs pulse length (approximately 45°), 2.00 s acquisition time, and 1.00 s relaxation delay. A 10 Hz line broadening was applied and all spectra were recorded at 25±0.2° C. All spectra were locked and referenced to an internal standard containing 0.2% solution of 4-fluorotoluene in toluene-d$_8$ (set at −120.771 ppm referenced from trifluorotoluene at −65.000 ppm). The common practice of adding D$_2$O to the buffer was avoided due to a noticeable deuterium isotope effect on $^{19}$F chemical shift. In vivo samples contained 0.4 mL washed cell paste and 0.1 mL PBS buffer. Additions to NMR samples came from buffered stocks, and the total volume of solutions added was always less than 2% of the total sample volume. Reduced NTR samples were prepared by the addition of NADH, and subsequent oxidation by addition of menadione in an argon environment to prevent noticeable NTR-FMN oxidation by oxygen. It is straightforward to ensure NTR protein is fully reduced because the samples change from bright yellow to colorless due to a reduction of FMN. While all spectral sets shown are from the same enzyme preparation, protein samples were run at least twice from different enzyme preparations to confirm the reproducibility of the $^{19}$F resonances. All purified protein samples were at 0.1 mM with the exception of the denatured samples. Denatured samples contained 0.05 mM protein, 4.2 M guanidinum-HCl at pH 7.8 and were heated to 70° C. for 5 min to ensure complete denaturation. Completely bound FMN-protein samples were generated by incubating pure protein with 100 µM FMN for 1-2 weeks at room temperature.

For NTR kinetics studies, assays were performed spectrophotometrically in the presence of 10 mM Tris-HCl buffer, pH 7.8, 150 µM NADH and varying amounts of menadione (10-700 µM). DMSO was used to prepare a 100 mM stock solution of menadione. For menadione, the reaction was initiated with 10 µl of NTR to give a final concentration of 2 nM. The progress of the reaction was monitored at 340 nm by observing the oxidation of NADH. This was converted to a rate of reduction of menadione using the molar absorbance of NADH ($\epsilon$=6200 M$^{-1}$ cm$^{-1}$), assuming 2 mol of NADH are consumed per mol reduced menadione and normalized for enzyme concentration. The observed rates (the observed slope of the reaction for 1 min) as a function of substrate concentration were fitted to a hyperbolic curve to generate k$_{cat}$ values for the data. For nicotinic acid inhibition studies, nicotinic acid concentrations of 7.5 µM and 30 µM were used, menadione was maintained at 400 µM while NADH was varied from 5-500 µM.

Incorporation of additional $^{19}$F-amino acids with the tfmPhe synthetase. Using the synthetase evolved to selectively incorporate tfmPhe, other $^{19}$F amino acids of similar shape and electrostatics may be incorporated site-specifically into proteins. By replacing tfpPhe in the media with 4-methyl-3-fluorophenylalanine (4) when expressing protein that would normally incorporate tfmPhe site-specifically in response to a TAG codon, 4 was incorporated in the location coded by TAG instead of tfpPhe.

Analysis of incorporation of 4-methyl-3-fluorophenylalanine (mf-Phe) into protein response to a TAG stop codon in *E. coli* with evolved tfmPhe MjTyrRS/tRNATyrCUA by SDS-PAGE. Silver-stained gel of purified NTR samples by immobilized metal affinity chromatography showed that when 4-methyl-3-fluorophenylalanine (4) was added to the media, full length HDH was produced containing 4; that when the unnatural amino acid was withheld, negligible HDH was detectable by silver stain after SDS-PAGE; and that when tfmPhe was added to the media, full length HDH (protein histidinol dehydrogenase) was produced containing tfmPhe.

Incorporation of additional $^{19}$F amino acids with p-benzoyl-phenylalanine (pBpa) synthetase. Using a synthetase known to selectively incorporate pBpa (SEQ ID NO: 7), other ¹⁹F amino acids of similar shape and electrostatics may be incorporated site-specifically into proteins. In media containing p-fluorobenzoylphenylalanine (pfBpa, 7) and an expression system responsive to a TAG codon, 7 was incorporated in the location coded by TAG.

Analysis of incorporation of p-fluorobenzoylphenylalanine into protein response to a TAG stop codon in *E. coli* with evolved pBpa MjTyrRS/tRNA TyrCUA by SDS-PAGE. Silver-stained gel of purified NTR samples by immobilized metal affinity chromatography showed that when pBpa was added to the media, full length HDH was produced containing pBpa; that when pfBpa was added to the media, full length HDH was produced containing pfBpa; and that when unnatural amino acid was withheld, no HDH was detectable by silver stain after SDS-PAGE.

By replacing pBpa in the media with 2',6'-difluoro-p-benzoylphenylalanine (dfBpa, 6), this fluorinated amino acid was incorporated in the location coded by TAG instead of pBpa. The pBpa MjTyrRS/tRNATyrCUA pair incorporated 6 less effectively than pBpa or 7 as seen by lower protein yield. To improve the incorporation efficiency of dfBpa, the active site of pBpa MjTyrRS was altered to better accommodate the slightly larger dfBpa amino acid. Amino acids in the active site (Ser159, Leu65) were reduced in size or reduced in polarity to better accept dfBpa. The modified pBpa synthetase (SEQ ID NO: 8) contained mutations Ser159Ala and Leu65Val and incorporated both dfBpa and pBpa with high efficiency.

Analysis of fluorinated pBpa-protein by SDS-PAGE. Analysis of incorporation of dfBpa (6) into HDH-225 in response to a TAG stop codon in *E. coli* with pBpa MjTyrRS/tRNATyrCUA by silver-stained gel of purified HDH samples by immobilized metal affinity chromatography showed that when dfBpa is added to the media, full length HDH was produced containing dfBpa; that when pBpa was added to the media full length HDH was produced containing pBpa; that when unnatural amino acid was withheld HDH was not produced. SDS-PAGE analysis of incorporation of dfBpa into HDH-225 in response to a TAG stop codon in *E. coli* with modified pBpa MjTyrRS/tRNATyrCUA by silver-stained gel of purified HDH samples by immobilized metal affinity chromatography showed that when dfBpa was added to the media full, length HDH was produced containing dfBpa; that when pBpa was added to the media, full length HDH was produced containing pBpa; and that when unnatural amino acid was withheld, HDH was not produced.

The amino acid pBpa in a protein may be used to determine the structural organization of the protein and conformational changes by initiating crosslinking with nearby peptides via externally provided ultraviolet irradiation. Fluorinated pBpa variants (6 and 7) were shown to crosslink upon irradiation. The time course of HDH-225pBpa and HDH-225-dfBpa during irradiation was studied by SDS-PAGE. Identical concentration of purified pBpa-HDH and dfBpa-HDH protein were silver-stained after separation by SDS-PAGE, which showed that the single cross-linked dimer migrates at dimer molecular weight (120 kDa), whereas the double cross-linked dimer migrates with an apparent molecular weight of 150 kDa.

To verify that discrete incorporation of each fluorinated amino acid only takes place at a specific site, a pure fluorinated protein was digested by trypsin and the fragments were analyzed by LC-ESI MS. The only peptide fragment containing the desired change was the expected F(X)ADMHR fragment with a minimum of >50% sequence coverage for all protein samples (MS/MS, Mascot search). These results along with the SDS-PAGE gel analysis confirmed the high fidelity and efficiency of fluorinated amino acid incorporation into proteins with the pDule plasmids.

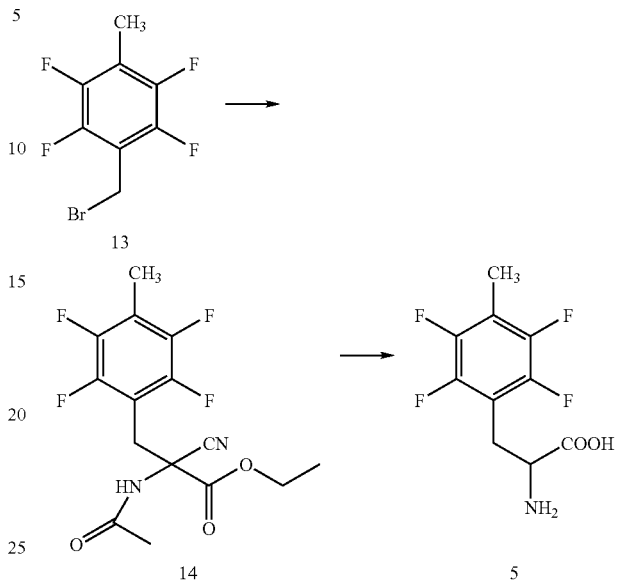

Synthesis of ethyl α-acetamido-α-cyano-β-(4-methyl-2,3,5,6-tetrafluorophenyl)-DL-propionate (14). A mixture of 500 mg (1.95 mmol) of compound 13, 497 mg (2.93 mmol) of ethyl acetamidocyanoacetate, 51 mg of 18-crown-6 in 20 mL $CH_3CN$, and 807 mg (5.85 mmol) of $K_2CO_3$ were stirred at room temperature under argon for 3 hours. The solution was filtered through the Celite® cake. The filtrate was concentrated and then allowed to dry under high vacuum. The crude product washed with hexane to remove brown impurities and dried under low pressure. The yield was 91%. Rf=0.4 (ethyl Acetate/hexane; 50:50). ¹H-NMR ($CDCl_3$): δ 4.40-4.25 (m, 2H, methylene of ethyl ester), 3.70 and 3.60 (dd, 2H, hydrogens on Cβ), 3.60 (singlet, 3H, methyl), 2.05 (s, 3H, methyl of ketone), 1.3 (triplet, 3H, ester methyl). ¹³C-NMR: 170.2, 165.2 (carbonyl); 146.0, 144.1, 117.1, 108.2 (aromatic); 115.3.0 (nitrile); 70.0, 64.3, 56.6, 22.5, 13.6 (alkyl). ¹⁹F-NMR: δ −145.0 ppm, δ −144.5 ppm.

Synthesis of 4-methyl-2,3,5,6-tetrafluorophenylalanine (5). A mixture of 0.6 g of compound 14 and 20 mL of a 1:1 solution of 8M HCl and trifluoroacetic acid was stirred at 180° C. for 24 hours. The reaction mixture was lyophilized to collect the crude product. Lingering trifluoroacetate ion was exchanged for chloride ion by suspending the crude product in ~20 mL 1 M HCl and lyophilizing the resulting solution. The product was then dissolved in 1 M NaOH and filtered. The clear solution was adjusted to a pH of 7 by addition of 1 M HCl and the precipitate was collected and washed twice with cold water. The remaining white solid was dried under high vacuum to obtain ~400 mg of a white powder. ¹H-NMR $D_2O$: δ 4.17 (t, 1H, $CHCH_2$), 3.56 (s, 3H, $CH_3$), 3.31 (dd, 1H, CHCHACHB), 2.23 (dd, 1H, CHCHACHB). ¹³C-NMR: δ 170.7 (carboxylic), 145.4, 143.5, 116.4, 109.3, 69.3, 52.0, 23.1. ¹⁹F-NMR: δ −146.8 ppm (dd, 2F), δ −147.7 ppm (dd, 2F). MS ES (cal. 251.0) pos. ion 252.0, neg. ion 250.0.

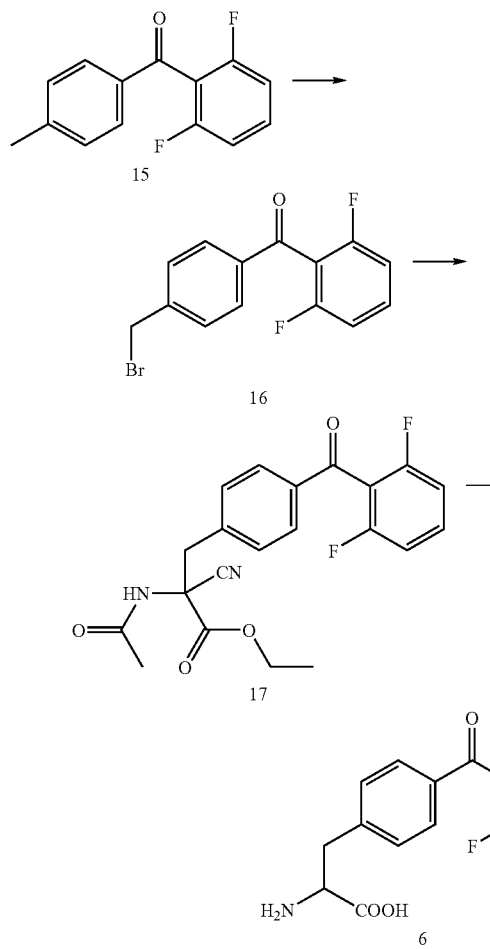

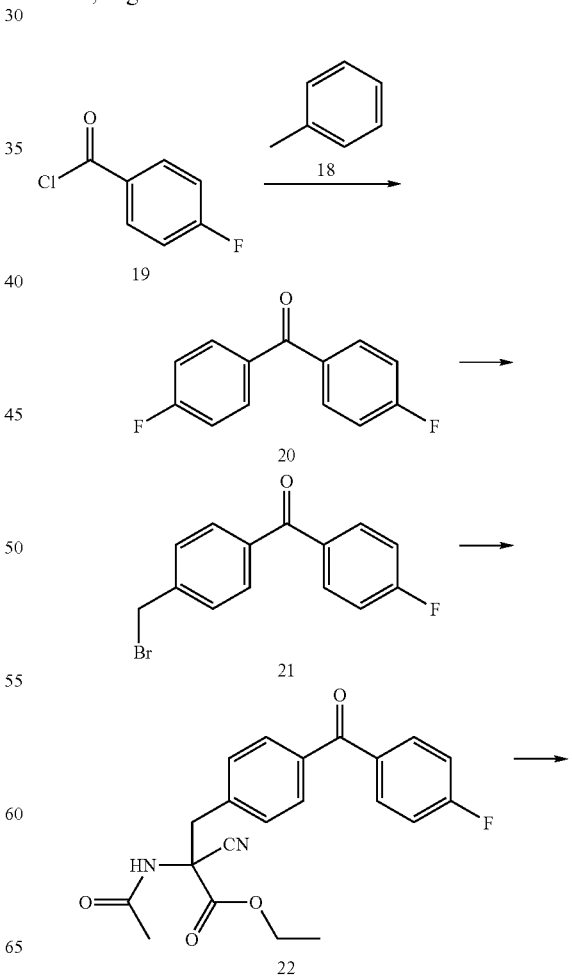

brown impurities and dried under low pressure. The yield was 56%. Rf=0.15 (ethyl acetate/hexane; 50:50). $^1$H-NMR: δ 7.83 (d, 2H, aromatic), 7.48 (t, 1H, aromatic), 7.41 (d, 2H, aromatic), 7.01 (d, 2H, aromatic), 6.90 (s, 1H, —NH), 4.30-4.05 (m, 2H, methylene of ethyl ester), 3.60 and 3.50 (dd, 2H, hydrogens on Cβ), 2.05 (s, 3H, methyl of ketone), 1.22 (doublet of triplets, 3H, ester methyl). $^{13}$C-NMR: δ 188.6, 170.1, 165.3 (carbonyl); 160.7, 158.7, 138.4, 136.7, 132.3, 130.6, 130.0, 111.9 (aromatic); 77.0 (aromatic C—F), 64.0, 57.4, 41.3, 22.6, 13.7 (alkyl).

Synthesis of 2',6'-difluoro-p-benzoyl-phenylalanine (6). A mixture of 0.12 g of compound 17 and 10 mL of a 1:1 solution of 8M HCl and trifluoroacetic acid was stirred at 150° C. for 24 hours. The reaction mixture was lyophilized to collect the crude product. Remaining trifluoroacetate ion was exchanged for chloride ion by suspending the crude product in ~20 mL 1 M HCl and lyophilizing the resulting solution. The product was then dissolved in 1 M NaOH and filtered. The clear solution was adjusted to a pH of 7 by addition of 1 M HCl and the precipitate was collected and washed twice with cold water. The remaining white solid was dried under high vacuum to obtain 50 mg of a white powder. $^1$H-NMR: δ 7.71 (d, 2H, aromatic), 7.67 (t, 1H, aromatic), 7.47 (d, 2H, aromatic), 7.29 (t, 2H, aromatic), 3.44 (dd, 3H, NH$_3^+$), 3.31 (m, 1H, CHCH$_2$), 3.21 (dd, 1H, CHCHACHB), 2.95 (dd, 1H, CHCHACHB). $^{13}$C-NMR: δ 188.2 (carbonyl); 168.8 (carboxylic); 161.2, 159.2, 157.7, 145.8, 134.4, 130.4, 129.3, 112.3 (aromatic); 55.0 (alkyl). MS ES (cal. 305.0) pos. ion 306.1, neg. ion 304.1

Synthesis of 4-bromomethyl-2', 6'-difluorobenzophenone (16). A mixture of 233 mg (1 mmol) of 4-methyl-2',6'-difluorobenzophenone, 178 mg (1 mmol) of recrystallized N-bromosuccinimide, 17 mg benzoyl peroxide, and 3 mL CCl$_4$ were refluxed under argon for 3 hours. The hot solution was filtered through a glass sintered filter and rinsed with 20 mL of hot CCl$_4$ until the crystals became colorless. The crystals were washed with 6 mL of cold CCl$_4$ and the solution was concentrated under vacuum. The crude product was purified by column chromatography on a silica gel flash column (13 cm×55 mm) eluted with ethyl acetate/hexane (15:85) and then concentrated under vacuum. The product was allowed to dry under high vacuum overnight. The resultant yield was 55%. Rf=0.3 (ethyl Acetate/hexane; 15:85). $^1$H-NMR: δ 7.84 (d, 2H, aromatic), 7.50 (d, 2H, aromatic), 7.46 (t, 1H, aromatic), 7.01 (m, 2H, aromatic), 4.51 (s, 2H). $^{13}$C-NMR (CDCl$_3$): δ 188.1 (carbonyl); 160.8, 158.8, 143.9, 136.6, 132.0, 130.0, 129.4, 111.9 (aromatic), 31.8 (alkyl bromide).

Synthesis of ethyl α-acetamido-α-cyano-β-(2', 4'-difluoro-4-benzophenone)-DL-propionate (17). A mixture of 172 mg (0.55 mmol) of compound 16, 142 mg (0.83 mmol) of ethyl acetamidocyanoacetate, 15.8 mg (0.06 mmol) 18-crown-6 in 8 mL CH$_3$CN, and 231 mg (1.67 mmol) of K$_2$CO$_3$ were stirred at room temperature under argon for 3 hours. The solution was filtered through a Celite® cake. The filtrate was concentrated and then allowed to dry under high vacuum. The crude product washed with hexane to remove

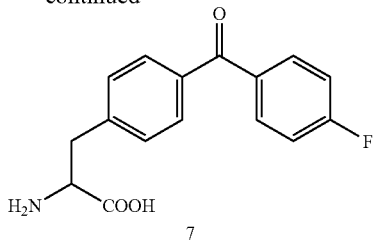

Synthesis of 4-methyl-4'-fluorobenzophenone (20). Aluminum chloride (3.74 g, 28 mmol) was added into a stirred solution of toluene 18 (60 mL) and 4-fluorobenzoyl chloride (3.42 g, 21.6 mmol). The solution was stirred at room temperature for 90 minutes, and then 5 mL of water was added dropwise to quench the reaction. The reaction mixture washed with water and 10% NaHCO$_3$. The solution was then dried with anhydrous MgSO$_4$. The solvent was removed from the solution to obtain a yellow solid. The yellow crude product was dissolved in a small amount of methylene chloride and hexane was added dropwise until precipitation occurred. The solution was then heated and the product was allowed to recrystallize to form 2.70 g of product (62% yield). $^1$H-NMR: δ 7.80 (dd, aromatic, 2H), 7.67 (d, aromatic, 2H), 7.26 (d, aromatic, 2H), 7.15 (t, aromatic, 2H), 2.42 (s, methyl, 3H). $^{13}$C-NMR: δ 195.0 (carbonyl); 166.2, 164.2, 143.3, 134.7, 132.2, 130.1, 129.0, 115.3 (aromatic); 21.6 (alkyl). $^{19}$F-NMR: δ −109.1 ppm.

Synthesis of 4-bromomethyl-4'-fluorobenzophenone (21). A mixture of 2.0 g (9.9 mmol) of 4-methyl-4'-fluorobenzophenone, 1.524 g (9.9 mmol) of recrystallized N-bromosuccinimide, 170 mg benzoyl peroxide, and 20 mL CCl$_4$ was refluxed under argon for 3 hours. The hot solution was filtered through a glass sintered filter and rinsed with 20 mL of hot CCl$_4$ until the crystals became colorless. The crystals were washed with 6 mL of cold CCl$_4$ and the solution was concentrated under reduced vacuum. The crude product was recrystallized from hexane and dried under vacuum. The resultant yield was 43%. Rf=0.25 (ethyl Acetate/hexane; 15:85). $^1$H-NMR: δ 7.85 (dd, aromatic, 2H), 7.75 (d, aromatic, 2H), 7.51 (d, aromatic, 2H), 7.17 (dd, aromatic, 2H), 4.52 (s, methyl, 3H). $^{13}$C-NMR: δ 195.0 (carbonyl); 166.5, 164.5, 142.5, 138.5, 133.4, 130.4, 129.2, 115.8, 115.5 (aromatic); 31.1 (alkyl).

Synthesis of ethyl α-acetamido-α-cyano-β-(4-fluoro-4-benzophenone)DL-propionate (22). A mixture of 600 mg (2.13 mmol) of compound 21, 545 mg (3.2 mmol) of ethyl acetamidocyanoacetate, 56 mg of 18-crown-6 in 8 mL CH$_3$CN, and 883 mg (6.4 mmol) of K$_2$CO$_3$ were stirred at room temperature under argon for 3 hours. The solution was filtered through a Celite® cake. The filtrate was concentrated and then allowed to dry under high vacuum. The crude product washed with hexane to remove brown impurities and dried under low pressure. The yield was 56%. Rf=0.15 (ethyl acetate/hexane; 50:50). $^1$H-NMR: δ 7.85 (dd, aromatic, 2H), 7.75 (d, aromatic, 2H), 7.38 (d, aromatic, 2H), 7.18 (dd, aromatic, 2H), 4.25-4.15 (m, 2H, methylene of ethyl ester), 3.60 and 3.50 (dd, 2H, hydrogens on Cβ), 3.62 (s, 3H, methyl), 1.22 (doublet of triplets, 3H, ester methyl). $^{13}$C-NMR: δ 194.7, 170.5, 165.7 (carbonyl); 137.3, 136.7, 133.4, 132.6, 132.5, 130.3, 130.1, 116.3, 115.7, 115.5, 70.0, 58.0, 22.4, 13.8.

Synthesis of 4-fluoro-p-benzoyl-phenylalanine (7). A mixture of 0.40 g of compound 22, and 30 mL of a 1:1 solution of 8M HCl and trifluoroacetic acid was stirred at 180° C. for 24 hours. The reaction mixture was lyophilized to collect the crude product. Remaining trifluoroacetate ion was exchanged for chloride ion by suspending the crude product in ~20 mL 1 M HCl and lyophilizing the resulting solution. The product was then dissolved in 1 M NaOH and filtered. The clear solution was adjusted to a pH of 7 by addition of 1 M HCl and the precipitate was collected and washed twice with cold water. The remaining white solid was dried under high vacuum to obtain ~180 mg of a white powder. $^1$H-NMR DMSO: δ 7.8 (dd, aromatic, 2H), 7.6 (d, aromatic, 2H), 7.43 (d, aromatic, 2H), 7.38 (dd, aromatic, 2H), 3.44 (bs, 2H, NH$_2$), 3.45 (dd, 1H, CHCHACHB), 3.25 (dd, 1H, CHCHACHB), 3.0 (m, 1H, CHCH$_2$). $^{19}$F-NMR: δ −109.27 ppm. MS ES (cal. 287.0) pos. ion 288.1, neg. ion 286.1.

Synthesis of 4-ethyl-4'-nitro-3'-fluorobenzophenone (23). Aluminum chloride (0.90 g, 6.8 mmol) was added into a stirred solution of toluene (15 mL) and 4-nitro-3-fluorobenzoyl chloride (1.0 g, 5.2 mmol). The solution was stirred at room temperature for 60 minutes, and then 5 mL of water was added dropwise to quench the reaction. The reaction mixture washed with water and 10% NaHCO$_3$. The solution was then dried with anhydrous MgSO$_4$. The solvent was removed under reduced pressure to obtain a yellow solid. The yellow crude product was dissolved in a small amount of methylene chloride and hexane was added dropwise until precipitation occurred. The solution was then heated and the product was allowed to recrystallize to form 1.10 g of compound 24 (81% yield). $^1$H-NMR: δ 8.15 (dd, aromatic, 2H), 7.71 (d, aromatic, 2H), 7.68 (m, aromatic, 1H), 7.34 (d, aromatic, 2H), 2.44 (s, methyl, 3H). $^{13}$C-NMR: δ 193.0 (carbonyl); 156.2, 154.2, 145.0, 144.5, 133.0, 130.5, 129.5, 126.1, 125.5, 121.5, 115.3 (aromatic); 22.2 (alkyl).

Synthesis of 4-bromomethyl-4'-nitro-3'-fluorobenzophenone (25). A mixture of 1.1 g (4.2 mmol) of 4-methyl-4'-nitro-3'-fluorobenzophenone, 0.654 g of recrystallized N-bromosuccinimide, 60 mg benzoyl peroxide, and 20 mL CCl$_4$ were refluxed under argon for 3 hours. The hot solution was filtered through a glass sintered filter and rinsed with 20 mL of hot CCl$_4$, until the crystals became colorless. The crystals were washed with 6 mL of cold CCl$_4$ and the solution was concentrated under reduced pressure. The crude product was recrystallized from hexane and dried under vacuum. The resultant yield was 58%. $^1$H-NMR CDCl$_3$: δ8.18 (dd, aromatic, 2H), 7.78 (d, aromatic, 2H), 7.68 (m, aromatic, 1H), 7.56 (d, aromatic, 2H), 4.57 (s, methyl, 3H). $^{13}$C-NMR: δ 192.4 (carbonyl); 156.2, 154.0, 146.7, 144.5, 144.4, 143.7, 143.6, 135.0, 133.0 130.5, 126.5, 125.5, 119.7, 119.4 (aromatic); 31.7 (alkyl). $^{19}$F-NMR: δ −118.5 ppm.

Synthesis of Ethyl α-acetamido-α-cyano-β-(4'-nitro-3'-fluoro-4-benzophenone)DL-propionate (26). A mixture of 835 mg (2.47 mmol) of compound 25, 630 mg of ethyl acetamidocyanoacetate, 65 mg of 18-crown-6 in 15 mL CH$_3$CN, and 1.02 mg of K$_2$CO$_3$ were stirred at room temperature under argon for 3 hours. The solution was filtered through a Celite® cake. The filtrate was concentrated and then allowed to dry under high vacuum. The crude product washed with hexane to remove brown impurities and dried under low pressure. The yield was 95%. Rf=0.05 (ethyl acetate/hexane; 50:50). $^1$H-NMR CDCl$_3$: δ8.18 (dd, aromatic, 2H), 7.78 (d, aromatic, 2H), 7.68 (m, aromatic, 1H), 7.41 (d, aromatic, 2H), 4.35-4.20 (m, 2H, methylene of ethyl ester), 3.72 and 3.52 (dd, 2H, hydrogens on C$_\beta$), 3.62 (s, 3H, methyl), 1.32 (doublet of triplets, 3H, ester methyl). $^{13}$C-NMR: δ 1942.5, 171.2, 170.0 (carbonyl); 165.4, 136.7, 156.1, 154.0, 143.5, 138.1, 135.6, 130.4, 126.4, 125.5, 119.5, 115.7, 70.0, 60.4, 57.4, 22.7, 13.8. $^{19}$F-NMR: δ −118.5 ppm.

Synthesis of 4'-nitro-3'-fluoro-p-benzoyl-phenylalanine (27). A mixture of 1.0 g of compound 26 and 30 mL of a 1:1 solution of 8M HCl and trifluoroacetic acid was stirred at 180° C. for 18 hours. The reaction mixture was lyophilized to collect the crude product. Remaining trifluoroacetate ion was exchanged for chloride ion by suspending the crude product in ~20 mL 1 M HCl and lyophilizing the resulting solution. The product was then dissolved in 1 M NaOH and filtered. The clear solution was adjusted to a pH of 7 by addition of 1 M HCl and the precipitate was collected and washed twice with cold water. The remaining yellow solid was dried under high vacuum to obtain ~260 mg of a yellow powder. $^1$H-NMR DMSO: δ 8.25 (t, aromatic, 1H), 7.8 (d, aromatic, 1H), 7.65 (m, aromatic, 3H), 7.38 (dd, aromatic, 2H), 3.55 (m, 1H, CHCH$_2$), 3.25 (dd, 1H, CHCH$_A$CH$_B$), 3.25 (dd, 1H, CHCH$_A$CH$_B$). $^{13}$C-NMR: δ192.9, 169.6, 155.3, 153.2, 144.2, 144.0, 138.8, 133.8, 130.0, 123.0, 126.7, 125.7, 119.0, 118.9, 55.0, 36.9. $^{19}$F-NMR: δ −115.86 ppm. MS ES (cal. 332.0) pos. ion 333.1, neg. ion 331.1.

In like manner as the foregoing, the following additional fluorinated amino acids may be prepared by one of ordinary skill in the art according to the synthesis schemes below:

Scheme 1:

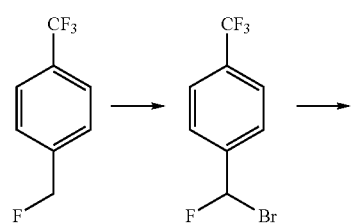

Scheme 2:

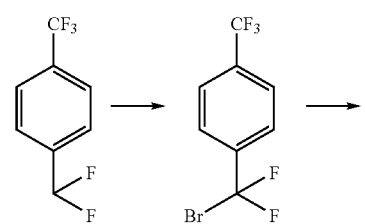

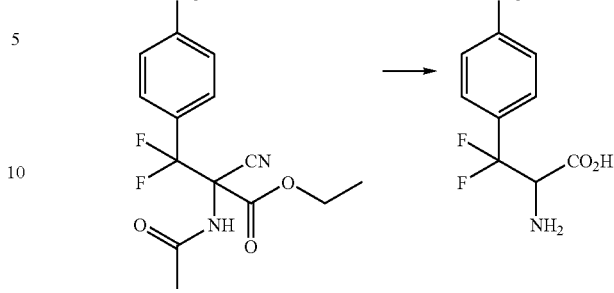

Scheme 3:

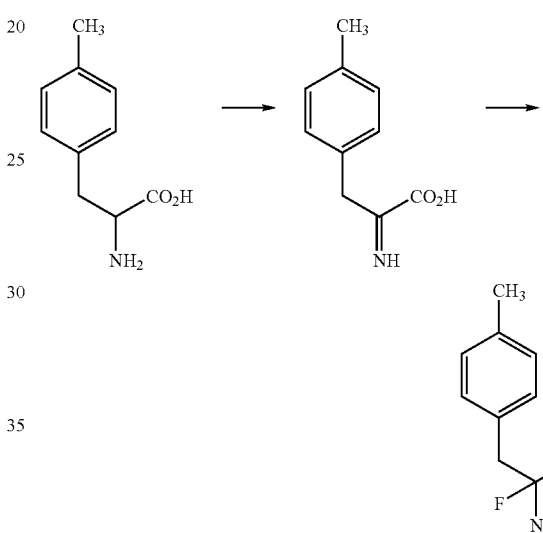

Scheme 4:

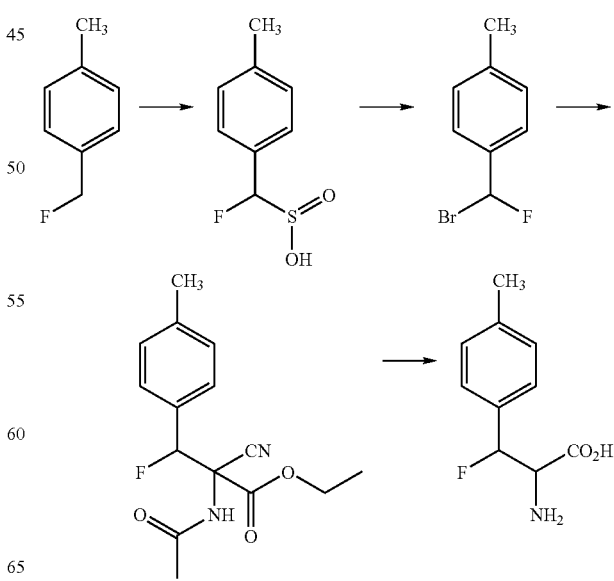

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiment, but that the invention will include all embodiments falling within the scope of the appended claims.

What is claimed is:

1. A method for making a fluorinated protein, comprising:
   (a) providing a nucleic acid, wherein the nucleic acid further includes a selector codon; and
   (b) providing a translation system, wherein the nucleic acid is translated by the translation system to encode a protein, and wherein the translation system further includes:
      (i) an orthogonal tRNA that recognizes the selector codon;
      (ii) a fluorinated aromatic amino acid comprising at least one fluorine atom and at least one lower alkyl group, wherein the at least one lower alkyl group is trifluoromethyl; and
      (iii) an orthogonal aminoacyl-tRNA synthetase that preferentially aminoacylates the orthogonal tRNA with the fluorinated amino acid to produce the fluorinated protein, wherein said orthogonal aminoacyl-tRNA synthetase is a polypeptide selected from the group consisting of polypeptides comprising the amino acid sequence as set forth in SEQ ID NO: 3 or SEQ ID NO: 8.

2. The method according to claim 1, wherein said orthogonal tRNA and said orthogonal aminoacyl-tRNA synthetase are complementary and said orthogonal aminoacyl-tRNA synthetase recognizes a selector codon.

3. The method according to claim 1, wherein $k_{cat}/K_m$ for aminoacylation of said orthogonal tRNA by said orthogonal aminoacyl-tRNA synthetase with said fluorinated aromatic amino acid is higher than $k_{cat}/K_m$ for aminoacylation of said orthogonal tRNA by said orthogonal aminoacyl-tRNA synthetase with a natural amino acid; said orthogonal aminoacyl-tRNA synthetase aminoacylates said orthogonal tRNA with said fluorinated aromatic amino acid at least ten-fold more efficiently than said orthogonal aminoacyl-tRNA synthetase aminoacylates said orthogonal tRNA with a natural amino acid; or said orthogonal tRNA is aminoacylated by an endogenous tRNA synthetase of a prokaryotic cell with reduced efficiency as compared to aminoacylation of endogenous tRNA by said endogenous tRNA synthetase.

4. The method according to claim 1, wherein said fluorinated aromatic amino acid comprises at least one $^{19}F$ atom.

5. The method according to claim 1, wherein said fluorinated aromatic amino acid comprises a photocrosslinking moiety or a photolabile group.

6. The method according to claim 1, wherein said fluorinated aromatic amino acid is a fluorinated compound selected from the group consisting of fluorinated phenylananine, fluorinated p-methylphenylalanine, and fluorinated p-benzoylphenylalanine, wherein at least one carbon atom of said fluorinated compound is substituted with a trifluoromethyl.

7. The method according to claim 1, wherein said fluorinated amino acid is a compound according to the following formula:

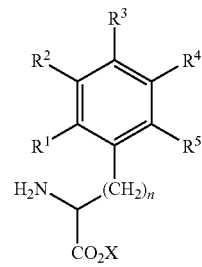

wherein n=0, 1, 2, or 3; X is $H^+$ or a biologically compatible cationic group; and $R^1$, $R^2$, $R^3$, $R^4$, and $R^5$ are selected from the group consisting of hydrogen, fluorine, lower alkyl groups, and fluorine-substituted lower alkyl groups, wherein at least one of $R^1$, $R^2$, $R^3$, $R^4$, $R^5$ is a trifluoromethyl.

8. The method according to claim 1, wherein said fluorinated amino acid is a compound according to the following formula:

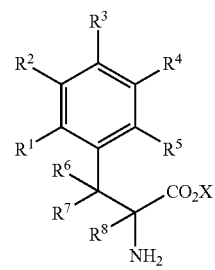

wherein X is $H^+$ or a biologically compatible cationic group; and $R^1$, $R^2$, $R^3$, $R^4$, $R^5$, $R^6$, $R^7$, and $R^8$ are selected from the group consisting of hydrogen, fluorine, lower alkyl groups, and fluorine-substituted lower alkyl groups, wherein at least one of $R^1$, $R^2$, $R^3$, $R^4$, $R^5$ is a trifluoromethyl.

9. The method according to claim 1, wherein said fluorinated amino acid is selected from the group consisting of:

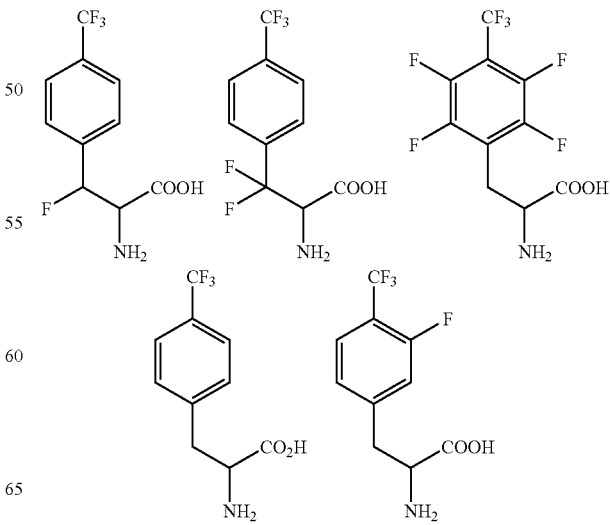

-continued
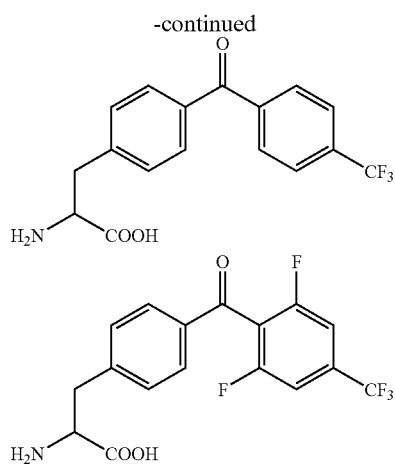
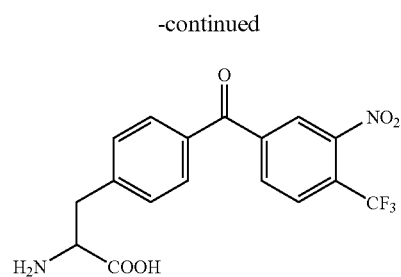
and biologically compatible salts thereof.
* * * * *